(12) United States Patent
Nuñez et al.

(10) Patent No.: US 10,870,731 B2
(45) Date of Patent: Dec. 22, 2020

(54) METHOD FOR END-CAPPING A POLYSILOXANE PREPOLYMER

(71) Applicant: Bausch & Lomb Incorporated, Rochester, NY (US)

(72) Inventors: Ivan M. Nuñez, Penfield, NY (US); Katie L. Poetz, Webster, NY (US); Andrew J. Hoteling, Ontario, NY (US); Joseph W. Hoff, Fairport, NY (US); Lynn Coullard, Williamson, NY (US); Analuz Mark, Spencerport, NY (US); Keyla M. Cubi, Rochester, NY (US); Joseph A. McGee, Canandaigua, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 0 days.

(21) Appl. No.: 16/246,715

(22) Filed: Jan. 14, 2019

(65) Prior Publication Data
US 2019/0233593 A1    Aug. 1, 2019

Related U.S. Application Data

(60) Provisional application No. 62/622,346, filed on Jan. 26, 2018.

(51) Int. Cl.
| | | |
|---|---|---|
| *C08G 77/38* | (2006.01) | |
| *C08L 83/08* | (2006.01) | |
| *G02B 1/04* | (2006.01) | |
| *A61L 27/18* | (2006.01) | |
| *C08G 77/20* | (2006.01) | |
| *C08G 77/26* | (2006.01) | |
| *C08G 77/388* | (2006.01) | |
| *A61F 2/16* | (2006.01) | |

(52) U.S. Cl.
CPC .............. *C08G 77/38* (2013.01); *A61L 27/18* (2013.01); *C08G 77/20* (2013.01); *C08G 77/26* (2013.01); *C08G 77/388* (2013.01); *C08L 83/08* (2013.01); *G02B 1/043* (2013.01); *A61F 2/16* (2013.01)

(58) Field of Classification Search
CPC .... C08G 77/38; C08G 77/382; C08G 77/385; C08F 30/08; C08F 230/08
USPC ........................................................ 526/279
See application file for complete search history.

(56) References Cited

U.S. PATENT DOCUMENTS

| | | | | |
|---|---|---|---|---|
| 4,605,712 A | * | 8/1986 | Mueller ................. | G02B 1/043 525/474 |
| 2003/0216536 A1 | | 11/2003 | Levandoski et al. | |
| 2012/0088843 A1 | | 4/2012 | Chang et al. | |
| 2014/0135408 A1 | * | 5/2014 | Wang .................... | C07F 7/1804 514/772.4 |
| 2018/0251587 A1 | * | 9/2018 | Lee ........................... | C09J 4/06 |

FOREIGN PATENT DOCUMENTS

| | | | |
|---|---|---|---|
| JP | 2017105753 A | | 6/2017 |
| WO | WO 2018/021674 | * | 2/2018 |

OTHER PUBLICATIONS

Sidney W. Benson, "The Induction Period in Chain Reactions". The Journal of Chemical Physics, Oct. 1952, vol. 20, No. 10, pp. 1605-1612.

* cited by examiner

*Primary Examiner* — Marc S Zimmer
(74) *Attorney, Agent, or Firm* — Ryan, Mason & Lewis, LLP

(57) ABSTRACT

A method is disclosed which involves the steps of (a) reacting a polysiloxane prepolymer having reactive functional end groups with a non-free radical polymerizable reactive end-capping agent; and (b) reacting the reaction product of step (a) with a free radical polymerizable reactive end-capping agent.

23 Claims, No Drawings

METHOD FOR END-CAPPING A POLYSILOXANE PREPOLYMER

BACKGROUND

1. Technical Field

The present invention generally relates to a method for end-capping a polysiloxane prepolymer and its use in making biomedical devices.

2. Description of the Related Art

Hydrogels represent a desirable class of materials for the manufacture of various biomedical devices, including contact lenses. A hydrogel is a hydrated cross-linked polymeric system that contains water in an equilibrium state. Hydrogel lenses offer desirable biocompatibility and comfort. The inclusion of a silicon-containing material in the hydrogel formulation generally provides higher oxygen permeability since silicon based materials have higher oxygen permeability than water.

In making silicone-containing biomedical devices, a polysiloxane prepolymer is typically used as a crosslinking agent. Various methods have been used in making the polysiloxane prepolymer. One such reaction is based on a well-known esterification procedure which involves the use of methacryloyl chloride as an endcapping agent. By employing the more reactive methacryloyl chloride, makes use of the catalyst, N,N-dimethylaminopyridine (DMAP) optional. However, methacryloyl chloride is a strong lachrymator and releases HCl upon exposure to moisture, making it more hazardous to handle. In addition, methacryloyl chloride tends to form dimers which then must be removed prior to use.

Accordingly, it would be desirable to provide an improved method for end-capping a polysiloxane prepolymer in a simple, cost effective manner that does not involve the use of methacryloyl chloride.

SUMMARY

In accordance with one embodiment of the present invention, there is provided a method comprising the steps of:

(a) reacting a polysiloxane prepolymer having reactive functional end groups with a non-free radical polymerizable reactive end-capping agent; and (b) reacting the reaction product of step (a) with a free radical polymerizable reactive-end-capping agent.

In accordance with a second embodiment of the present invention, there is provided a method comprising the step of:

(a) reacting a polysiloxane prepolymer of formula I

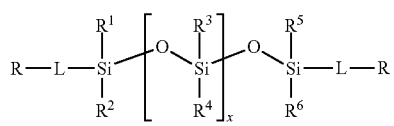

wherein R, $R^1$-$R^6$ and L are as defined herein with a non-free radical polymerizable reactive end-capping agent; and (b) reacting the reaction product of step (a) with a free radical polymerizable reactive end-capping agent having ethylenically unsaturated reactive end groups.

The present invention is based on the surprising discovery that the modulus of the resulting polysiloxane prepolymer can be reduced by first reacting the polysiloxane prepolymer having reactive functional end groups with a minor amount of a non-free radical polymerizable reactive end-capping agent prior to reacting with a free radical polymerizable reactive end-capping agent. It is believed that the non-free radical polymerizable reactive end-capping agent will distribute itself in essentially a statistical fashion following a binomial function. After the non-free radical polymerizable reactive capping agent has reacted completely, the free radical polymerizable reactive end-capping agent is added in excess to ensure complete conversion of all the unreacted functional end groups of the polysiloxane prepolymer. In this manner, the resulting polysiloxane prepolymer is a product with binomially distributed free radical polymerizable reactive end groups and non-free radical polymerizable reactive end groups. This approach, in essence, controls the crosslink density in the resulting polysiloxane prepolymer. Thus, by varying the crosslinker concentration of resulting polysiloxane prepolymer in a biomedical device-forming formulation, e.g., a contact lens, the lens modulus can be lowered while also increasing its water content.

DETAILED DESCRIPTION

The present invention is directed to a method for making a polysiloxane prepolymer for use in preparing biomedical devices. In general, the method involves at least the steps of (a) reacting a polysiloxane prepolymer having reactive functional end groups with a non-free radical polymerizable reactive end-capping agent; and (b) reacting the reaction product of step (a) with a free radical polymerizable reactive end-capping agent.

In one embodiment, the polysiloxane prepolymer having reactive functional end groups for use in step (a) is of the general formula (I):

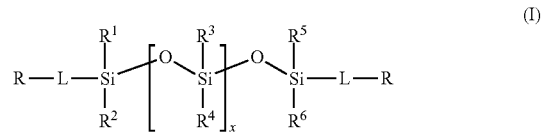

wherein each R is an independently reactive functional end group and includes a hydroxyl-containing reactive functional end group, and an amine-containing reactive functional end group, $R^1$ to $R^6$ are independently straight or branched, substituted or unsubstituted $C_1$-$C_{30}$ alkyl group, a substituted or unsubstituted $C_3$-$C_{30}$ cycloalkyl group, a substituted or unsubstituted $C_4$-$C_{30}$ cycloalkylalkyl group, a substituted or unsubstituted $C_3$-$C_{30}$ cycloalkenyl group, a substituted or unsubstituted $C_6$-$C_{30}$ aryl group, and a substituted or unsubstituted $C_7$-$C_{30}$ arylalkyl group, and L is independently a linking group.

A hydroxyl-containing reactive functional end groups for use herein is a group of the general formula —OH Representative examples of amine-containing reactive functional end groups for use herein include, by way of example, an amine having the following general formula —$NHR^7$ wherein $R^7$ is independently hydrogen or an alkyl group, aryl group, and cycloalkyl group as defined herein and the like.

Linking group L is independently a straight or branched alkyl group, cycloalkyl group, an aryl group, an ether or polyether group, and an ester group as defined herein.

Representative examples of alkyl groups for use herein include, by way of example, a straight or branched alkyl chain radical containing carbon and hydrogen atoms of from 1 to about 30 carbon atoms or from 1 to about 12 carbon atoms or from 1 to about 6 carbon atoms with or without unsaturation, to the rest of the molecule, e.g., methyl, ethyl, n-propyl, 1-methylethyl (isopropyl), n-butyl, n-pentyl, methylene, ethylene, etc., and the like.

Representative examples of cycloalkyl groups for use herein include, by way of example, a substituted or unsubstituted non-aromatic mono or multicyclic ring system of about 3 to about 30 carbon atoms or from 3 to about 6 carbon atoms such as, for example, cyclopropyl, cyclobutyl, cyclopentyl, cyclohexyl, perhydronapththyl, adamnantyl and norbornyl groups, bridged cyclic groups or sprirobicyclic groups, e.g., spiro-(4, 4)-non-2-yl and the like, optionally containing one or more heteroatoms, e.g., O and N, and the like.

Representative examples of cycloallkylalkyl groups for use herein include, by way of example, a substituted or unsubstituted cyclic ring-containing radical containing from about 4 to about 30 carbon atoms or from 3 to about 6 carbon atoms directly attached to the alkyl group which are then attached to the main structure of the monomer at any carbon from the alkyl group that results in the creation of a stable structure such as, for example, cyclopropylmethyl, cyclobutylethyl, cyclopentylethyl and the like, wherein the cyclic ring can optionally contain one or more heteroatoms, e.g., O and N, and the like.

Representative examples of cycloalkenyl groups for use herein include, by way of example, a substituted or unsubstituted cyclic ring-containing radical containing from about 3 to about 30 carbon atoms or from 3 to about 6 carbon atoms with at least one carbon-carbon double bond such as, for example, cyclopropenyl, cyclobutenyl, cyclopentenyl and the like, wherein the cyclic ring can optionally contain one or more heteroatoms, e.g., O and N, and the like.

Representative examples of aryl groups for use herein include, by way of example, a substituted or unsubstituted monoaromatic or polyaromatic radical containing from about 6 to about 30 carbon atoms such as, for example, phenyl, naphthyl, tetrahydronapthyl, indenyl, biphenyl and the like, optionally containing one or more heteroatoms, e.g., O and N, and the like.

Representative examples of arylalkyl groups for use herein include, by way of example, a substituted or unsubstituted aryl group as defined herein directly bonded to an alkyl group as defined herein, e.g., $-CH_2C_6H_5$, $-C_2H_4C_6H_5$ and the like, wherein the aryl group can optionally contain one or more heteroatoms, e.g., O and N, and the like.

Representative examples of ester groups for use herein include, by way of example, a carboxylic acid ester having one to 20 carbon atoms and the like.

Representative examples of ether or polyether containing groups for use herein include, by way of example, an alkyl ether, cycloalkyl ether, cycloalkylalkyl ether, cycloalkenyl ether, aryl ether, arylalkyl ether wherein the alkyl, cycloalkyl, cycloalkylalkyl, cycloalkenyl, aryl, and arylalkyl groups are as defined herein. Exemplary ether or polyether-containing groups include, by way of example, alkylene oxides, poly(alkylene oxide)s such as ethylene oxide, propylene oxide, butylene oxide, polyethylene oxide)s, poly-ethylene glycol)s, poly(propylene oxide)s, poly(butylene oxide)s and mixtures or copolymers thereof, an ether or polyether group of the general formula $-(R^{14}OR^{15})_t$, wherein $R^{14}$ is a bond, a substituted or unsubstituted alkyl, cycloalkyl or aryl group as defined herein and $R^{15}$ is a substituted or unsubstituted alkyl, cycloalkyl or aryl group as defined herein and t is at least 1, and the like.

Methods for making the polysiloxane prepolymers for use in step (a) of the method of present invention are well known and within the purview of one skilled in the art. In addition, the polysiloxane prepolymers are also commercially available from such sources as, for example, Gelest, Silar, Shin-Etsu, Momentive and Siltech, The non-free radical polymerizable reactive end-capping agents for reacting with the polysiloxane prepolymers in step (a) can be any non-free radical polymerizable reactive end-capping agent capable of being reacted with the polysiloxane prepolymers in step (a). In one embodiment, a non-free radical polymerizable reactive end-capping agent is a carbonyl-containing non-free radical polymerizable reactive end-capping agent of the general formula:

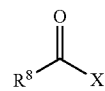

wherein $R^8$ is a non-reactive moiety and C(O)X is a non-free radical polymerizable reactive group. Suitable non-reactive moiety $R^8$ includes, for example, a hydrocarbon moiety such as a $C_1$ to $C_{18}$ hydrocarbon including, by way of example, a $C_1$ to $C_{18}$ alkyl moiety, a $C_3$ to $C_{18}$ cycloalkyl moiety and a $C_6$ to $C_{18}$ aryl moiety as defined herein. Suitable non-free radical polymerizable reactive groups C(O)X include those in which X is, for example, —OH, a halogen such as Cl, Br, F and I, and —OR$^9$ wherein $R^9$ is a substituted or unsubstituted heteroaryl or a —C(O)R$^8$ wherein $R^8$ has the aforestated meanings. Representative examples of heteroaryl groups include, by way of example, a substituted or unsubstituted stable 6 to about 30 membered ring radical, containing carbon atoms and from one to five heteroatoms, e.g., nitrogen, phosphorus, oxygen, sulfur and mixtures thereof, wherein the heterocyclic ring radicals may be a monocyclic, bicyclic or tricyclic ring system, which may include fused, bridged or spiro ring systems. In addition, the ring radical may be partially or fully saturated (i.e., heteroaromatic or heteroaryl aromatic). The substituents on the heteroaryl ring are leaving groups which allow the substituents to be exchanged with the reactive functional end groups of formula I. Suitable substituents can be, for example, $C_1$ to $C_6$ alkoxy groups, $C_1$ to $C_6$ fluoralkyl groups or $C_6$ to $C_{12}$ fluoroaryl groups. Accordingly, in one embodiment, examples of a carbonyl-containing non-free radical polymerizable reactive end-capping agent can be those of the general formulae:

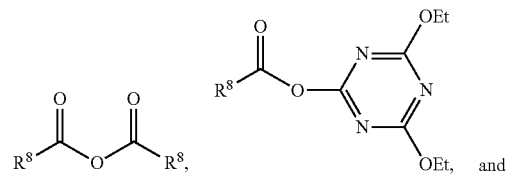

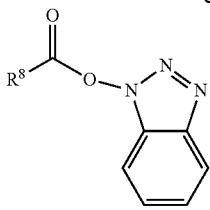

wherein R[8] has the aforestated meanings.

In one embodiment, a non-free radical polymerizable reactive end-capping agent is an isocyanate-containing non-free radical polymerizable reactive end-capping agent of the general formula R[8]—N═C═O wherein R[8] has the aforestated meanings.

In one embodiment, a non-free radical polymerizable reactive end-capping agent is a chloroformate of the general formula:

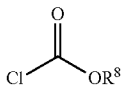

wherein R[8] has the aforestated meanings.

In general, the non-free radical polymerizable reactive end-capping agent is reacted with the polysiloxane prepolymer in a minor amount. In one embodiment, the non-free radical polymerizable reactive end-capping agent is reacted with the polysiloxane prepolymer in an amount ranging from about 1 to about 30 mole % or from about 2 to about 30 mole %, In one embodiment, the non-free radical polymerizable reactive end-capping agent is reacted with the polysiloxane prepolymer in an amount ranging from about 3 to about 15 mole %.

In one embodiment, the reaction of the non-free radical polymerizable reactive end-capping agent with the polysiloxane prepolymer can be carried out in the presence of a solvent such as a polar solvent. Suitable polar solvents include, for example, tetrohydrofuran, 1,4-dioxane, t-butyl-methyl ether, methylene chloride and chloroform.

In general, the solvent is ordinarily present in an amount ranging from about 75 to about 1000 mL. In one embodiment, the solvent is present in an amount of from about 600 to about 1000 mL.

In one embodiment, the reaction of the non-free radical polymerizable reactive end-capping agent with the polysiloxane prepolymer is generally carried out at a temperature ranging from about 0° C. to about 40° C. and at a pressure of up to about 0,8 bar to about 1.2 bar. In one embodiment, the reaction is carried out at a temperature ranging from about 25° C. to about 40° C. The time period for the reaction will ordinarily range from about 0.8 to about 1.2 hours. The reaction is typically carried out under atmospheric pressure.

The product of step (a) is then reacted with a free radical polymerizable reactive end-capping agent to form the end-capped polysiloxane prepolymer of the present invention. In one embodiment, a suitable free radical polymerizable reactive end-capping agent is a reactive end-capping agent having ethylenically unsaturated reactive end groups. In one embodiment, ethylenically unsaturated reactive end groups include by way of example, (meth)acrylate end groups, vinyl end groups, acrylamide end groups and the like. Representative examples of reactive end-capping agents include (meth)acrylate-containing reactive end-capping agents, vinyl-containing reactive end-capping agents, unsaturated acidic-containing reactive end-capping agents, styryl-containing reactive end-capping agents and the like. As used herein, the term "(meth)" denotes an optional methyl substituent. Thus, terms such as "(meth)acrylate" denotes either methacrylate or acrylate, and "(meth)acrylamide" denotes either methacrylamide or acrylamide.

Suitable (meth)acrylate-containing free radical polymerizable reactive end-capping agents for use herein include, for example, symmetrical (meth)acrylate-containing acid anhydride reactive end-capping agents, (meth)acrylate-containing acid chloride free radical polymerizable reactive end-capping agents, (meth)acrylate-containing carboxylic acid free radical polymerizable reactive end-capping agents, (meth)acrylate-containing carbonyl-containing free radical polymerizable reactive end-capping agents, (meth)acrylate-containing isocyanate-containing free radical polymerizable reactive end-capping agents and the like. In one embodiment, symmetrical (meth)acrylate-containing acid anhydride free radical polymerizable reactive end-capping agents include those of the formula:

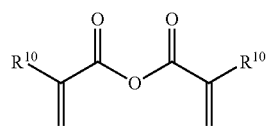

wherein R[10] is independently H (acrylate) or CH$_3$ (methacrylate).

In one embodiment, suitable (meth)acrylate-containing acid chloride free radical polymerizable reactive end-capping agents include those of the formula:

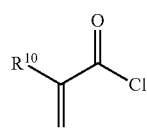

wherein R[10] has the aforestated meanings.

In one embodiment, suitable (meth)acrylate-containing carboxylic acid free radical polymerizable reactive end-capping agents include, for example, those of the formula:

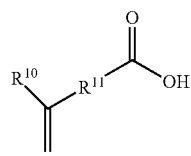

wherein R[10] has the aforestated meanings, and wherein R[11] is a C$_1$ to C$_6$ straight or branched alkylene group or a C$_6$ to C$_{12}$ substituted or unsubstituted arylene group.

In one embodiment, suitable (meth)acrylate-containing carbonyl-containing free radical polymerizable reactive end-capping agents include, for example, those of the formula:

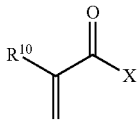

wherein $R^{10}$ has the aforestated meanings, and X is a reactive end group including by way of example, OH, a halogen such as Cl, Br, F and I, and —$OR^9$ wherein $R^9$ has the aforestated meanings.

In one embodiment, suitable (meth)acrylate-containing isocyanate-containing free radical polymerizable reactive end-capping agents include, for example, those of the formula:

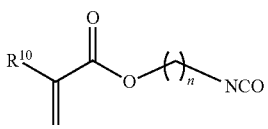

wherein $R^{10}$ has the aforestated meanings, and n is an integer from 1 to 6. Examples of such ethylenically unsaturated isocyanate-containing free radical polymerizable reactive end-capping agents include 2-isocyanatoethyl acrylate and 2-isocyanatoethyl methacrylate (TEM).

Suitable vinyl-containing free radical polymerizable free radical polymerizable reactive end-capping agents for use herein include, for example, vinyl isocyanate free radical polymerizable reactive end-capping agents, vinyl chloroformate free radical polymerizable reactive end-capping agents and the like. In one embodiment, a vinyl isocyanate free radical polymerizable reactive end-capping agent can be of the formula:

In one embodiment, a vinyl chloroformate free radical polymerizable reactive end-capping agent can be of the formula:

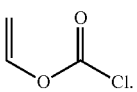

Suitable ethylenically unsaturated acidic-containing free radical polymerizable reactive end-capping agents include, for example, maleic anhydride, or a compound of the formula

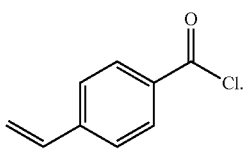

In one embodiment, other free radical polymerizable reactive end-capping agents include the esters discussed above for the non-free radical polymerizable reactive end-capping agents and having an ethylenically unsaturated reactive end group. In one embodiment, it is also contemplated of direct coupling of the corresponding acid with a dicarbodiimide ($R^1$—N=C=N—$R^2$) wherein $R^1$ and $R^2$ have the aforestated meanings is also possible.

In general, the free radical polymerizable reactive end-capping agent is reacted with the product of step (a) in an excess amount, i.e., an amount ranging from about 101 to about 200 mole %. In one embodiment, the free radical polymerizable reactive end-capping agent is reacted with the product of step (a) in an amount ranging from about 101 to about 125 mole %.

In one embodiment, the reaction of the free radical polymerizable reactive end-capping agent with the product of step (a) can be carried out in the presence of a solvent such as the polar solvents discussed above. In general, the solvent is ordinarily present in an amount ranging from about 75 to about 1000 mL. In one embodiment, the solvent is present in an amount of from about 600 to about 1000 mL.

The reaction of the free radical polymerizable reactive end-capping agent with the product of step (a) is generally carried out at a temperature ranging from about 0° C. to about 40° C. and at a pressure of up to about 0.8 bar to about 1.2 bar. In one embodiment, the reaction is carried out at a temperature ranging from about 25° C. to about 40° C. The time period for the reaction will ordinarily range from about 0.8 to about 1.2 hours.

Upon completion of the reaction, the final product is washed with an aqueous solution such as a 10% aqueous hydrochloric acid solution, 10% sodium bicarbonate solution, and a 5% sodium chloride solution. Next, the organic layer is separated and dried with a suitable drying agent to obtain the resulting polysiloxane prepolymer. Examples of a suitable drying agent include magnesium sulfate, and sodium sulfate.

The resulting polysiloxane prepolymer thus obtained from the method of present invention can then be advantageously reacted with one or more biomedical device-forming monomers to form a biomedical device. As used herein, a "biomedical device" is any article that is designed to be used while either in or on mammalian tissues or fluid, and preferably in or on human tissue or fluids. Representative examples of biomedical devices include, but are not limited to, artificial ureters, diaphragms, intrauterine devices, heart valves, catheters, denture liners, prosthetic devices, ophthalmic lens applications, where the lens is intended for direct placement in or on the eye, such as, for example, intraocular devices and contact lenses.

In embodiment, the biomedical device is an ophthalmic device, particularly contact lenses, most particularly contact lenses made from silicon hydrogels. As used herein, the term "ophthalmic device" and "lens" refer to devices that reside in or on the eye. These devices can provide optical correction, wound care, drug delivery, diagnostic functionality or cosmetic enhancement or effect or a combination of these properties. Useful ophthalmic devices include, but are not limited to, ophthalmic lenses such as soft contact lenses, e.g., a soft, hydrogel lens; soft, non-hydrogel lens and the like, hard contact lenses, e.g., a hard, gas permeable lens material and the like, intraocular lenses, overlay lenses, ocular inserts, optical inserts and the like. As is understood by one skilled in the art, a lens is considered to be "soft" if it can be folded back upon itself without breaking. The ophthalmic devices such as contact lenses of the present invention can be spherical, toric, bifocal, may contain cosmetic tints, opaque cosmetic patterns, combinations thereof and the like.

Generally, the biomedical device-forming comonomer contains at least one polymerizable group. In one embodiment, a suitable biomedical device-forming comonomer includes hydrophobic monomers, hydrophilic monomers and the like and mixtures thereof. Representative examples of hydrophilic comonomers include, but are not limited to, unsaturated carboxylic acids, such as methacrylic and acrylic acids; (meth)acrylic substituted alcohols or polyols such as 2-hydroxyethyl methacrylate, 2-hydroxyethyl acrylate, glyceryl methacrylate and the like; vinyl lactams such as N-vinylpyrrolidone and the like; and (meth)acrylamides such as methacrylamide, N,N-dimethylacrylamide and the like and combinations thereof. Still further examples are the hydrophilic vinyl carbonate or vinyl carbamate monomers disclosed in U.S. Pat. No. 5,070,215, and the hydrophilic oxazolone monomers disclosed in U.S. Pat. No. 4,910,277. Other suitable hydrophilic monomers will be apparent to one skilled in the art. The hydrophilic monomers can be present in the mixtures in an amount ranging from 0 to about 70 weight percent, based on the total weight of the mixture.

Suitable hydrophobic monomers include $C_1$ to $C_{20}$ alkyl and $C_3$ to $C_{20}$ cycloalkyl (meth)acrylates, substituted and unsubstituted $C_6$ to $C_{20}$ aryl (meth)acrylates, (meth)acrylonitriles, fluorinated alkyl methacrylates, long-chain acrylamides such as octyl acrylamide, and the like. The hydrophobic monomers can be present in the mixtures in an amount ranging from 0 to about 30 weight percent, based on the total weight of the mixture.

In one embodiment, the polysiloxane prepolymer obtained from the method of the present invention is used to form a soft contact lens such as those commonly referred to as silicon hydrogel lenses. Silicon hydrogels in general are a well-known class of materials that comprise hydrated, cross-linked polymeric systems containing water in an equilibrium state. Silicon hydrogels generally have water content greater than about 5 weight percent and more commonly between about 10 to about 80 weight percent. Such materials are usually prepared by polymerizing a mixture containing one or more silicon-containing biomedical device-forming monomers and at least one hydrophilic monomer together with the polysiloxane prepolymer obtained from the method of the present invention.

In general, silicon-containing biomedical device-forming monomers for use in the formation of silicon-containing biomedical devices such as hydrogels include silicon monomers containing one or more Si—O units as well as silicon monomers containing one or more silicon atoms with one or more Si—O units. In one preferred embodiment, a silicon monomer contains more than one Si—O unit to provide a lens having a desired oxygen permeability. Silicon-containing monomers are well known in the art and numerous examples are provided in U.S. Pat. Nos. 4,136,250; 4,153,641; 4,740,533; 5,034,461; 5,070,215; 5,260,000; 5,310,779; and 5,358,995. Representative examples of applicable silicon-containing monomeric units include bulky polysiloxanylalkyl (meth)acrylic monomers represented by the structure of Formula I:

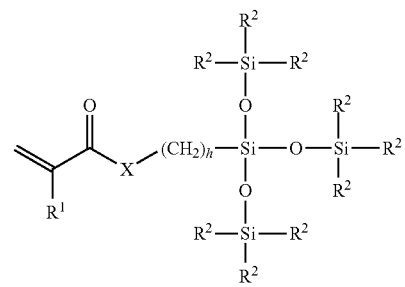

wherein X denotes —O— or —NR—; each $R^1$ independently denotes hydrogen or methyl, each $R^2$ independently denotes a lower alkyl radical, phenyl radical or a group represented by

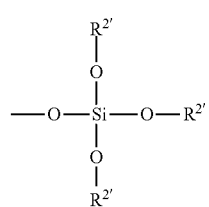

wherein each $R^{2'}$ independently denotes a lower alkyl or phenyl radical; and h is 1 to 10.

Examples of bulky monomers are 3-methacryloyloxypropyltris(trimethyl-siloxy)silane or tris(trimethylsiloxy)silylpropyl methacrylate, sometimes referred to as TRIS and tris(trimethylsiloxy)silylpropyl vinyl carbamate, sometimes referred to as TRIS-VC and the like.

Such bulky monomers may be copolymerized with a silicon macromonomer, such as a poly(organosiloxane) capped with an unsaturated group at two or more ends of the molecule. U.S. Pat. No. 4,153,641 discloses, for example, various unsaturated groups such as acryloyloxy or methacryloyloxy groups.

Another class of representative silicon-containing monomers includes, but is not limited to, silicon-containing vinyl carbonate or vinyl carbamate monomers such as, for example, 1,3-bis[4-vinyloxycarbonyloxy)but-1-yl]tetramethyl-disiloxane; 3-(trimethylsilyl)propyl vinyl carbonate; 3-(vinyloxycarbonylthio)propyl-[tris(trimethylsiloxy)silane]; 3-[tris(trimethylsiloxy)silyl]propyl vinyl carbamate; 3-[tris(trimethylsiloxy)silyl]propyl allyl carbamate; 3-[tris(trimethylsiloxy)silyl]propyl vinyl carbonate; t-butyldimethylsiloxyethyl vinyl carbonate; trimethylsilylethyl vinyl carbonate; trimethylsilylmethyl vinyl carbonate and the like and mixtures thereof.

Another class of silicon-containing monomers includes polyurethane-polysiloxane macromonomers (also sometimes referred to as prepolymers), which may have hard-soft-hard blocks like traditional urethane elastomers. They may be end-capped with a hydrophilic monomer such as 2-hydroxyethyl methacrylate (HEMA). Examples of such silicon-containing urethanes are disclosed in a variety or publications, including PCT Published Application No. WO 96/31792 discloses examples of such monomers, which disclosure is hereby incorporated by reference in its entirety.

Representative examples of silicon-containing urethanes are represented by Formulae II and III:

$$E(*D*A*D*G)_a*D*A*D*E'; \text{ or} \qquad (II)$$

$$E(*D*G*D*A)_a*D*A*D*E'; \text{ or} \qquad (III)$$

Ar denotes an aromatic radical having about 6 to about 30 carbon atoms;

w is 0 to 6; x is 0 or 1; y 0 or 1; and z is 0 or 1.

One preferred silicon-containing urethane is represented by Formula VI:

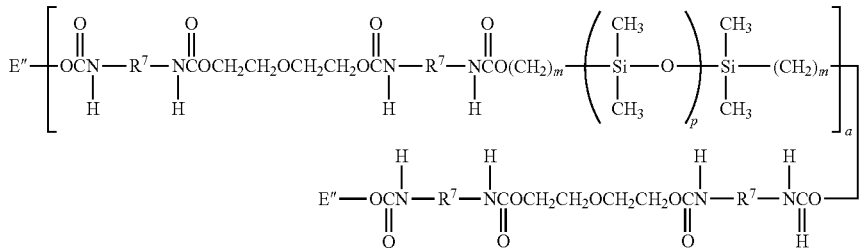
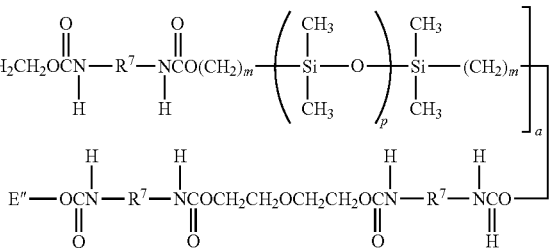

wherein:

D independently denotes an alkyl diradical, an alkyl cycloalkyl diradical, a cycloalkyl diradical, an aryl diradical or an alkylaryl diradical having 6 to about 30 carbon atoms;

G independently denotes an alkyl diradical, a cycloalkyl diradical, an alkyl cycloalkyl diradical, an aryl diradical or an alkylaryl diradical having 1 to about 40 carbon atoms and which may contain ether, thio or amine linkages in the main chain;

\* denotes a urethane or ureido linkage;

a is at least 1;

A independently denotes a divalent polymeric radical of Formula IV:

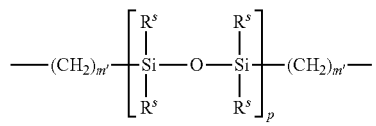

wherein each $R^5$ independently denotes an alkyl or fluoro-substituted alkyl group having 1 to about 10 carbon atoms which may contain ether linkages between the carbon atoms; m' is at least 1; and p is a number that provides a moiety weight of about 400 to about 10,000;

each of E and E' independently denotes a polymerizable unsaturated organic radical represented by Formula V:

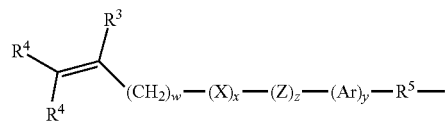

wherein: $R^3$ is hydrogen or methyl;

$R^4$ is hydrogen, an alkyl radical having 1 to 6 carbon atoms, or a —CO—Y—$R^6$ radical wherein Y is —O—, —S— or —NH—;

$R^5$ is a divalent alkylene radical having 1 to about 10 carbon atoms;

$R^6$ is a alkyl radical having 1 to about 12 carbon atoms;

X denotes —CO— or —OCO—;

Z denotes —O— or —NH—;

wherein m is at least 1 and is preferably 3 or 4, a is at least 1 and preferably is 1, p is a number which provides a moiety weight of about 400 to about 10,000 and is preferably at least about 30, $R^7$ is a diradical of a diisocyanate after removal of the isocyanate group, such as the diradical of isophorone diisocyanate, and each E" is a group represented by:

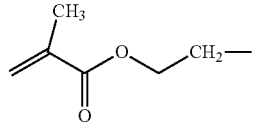

In another embodiment of the present invention, a silicon hydrogel material comprises (in bulk, that is, in the monomer mixture that is copolymerized) about 5 to about 70 percent, or from about 10 to about 60, by weight of one or more silicon macromonomers, about 5 to about 60 percent, or from about 10 to about 60 percent, by weight of one or more polysiloxanylalkyl (meth)acrylic monomers, and about 20 to about 60 percent, or from about 10 to about 50 percent, by weight of a hydrophilic monomer, in general, the silicon macromonomer is a poly(organosiloxane) capped with an unsaturated group at one or more ends of the molecule. In addition to the end groups in the above structural formulas, U.S. Pat. No. 4,153,641 discloses additional unsaturated groups, including a.cryloyloxy or methacryloyloxy groups. Fumarate-containing materials such as those disclosed in U.S. Pat. Nos. 5,310,779; 5,449,729 and 5,512,205 are also useful substrates in accordance with the invention. Preferably, the silicon-containing monomer is a silicon-containing vinyl carbonate or vinyl carbamate or a polyurethane-polysiloxane having one or more hard-soft-hard blocks and end-capped with a hydrophilic monomer. The silicon-containing monomers can be present in the mixtures in an amount ranging from 10 to about 75 weight percent, based on the total weight of the monomer mixture.

The above materials are merely exemplary silicon-containing monomers and have been disclosed in various publications and are being continuously developed for use in forming silicon-containing biomedical devices such as contact lenses. For example, a silicon-containing biomedical device for use herein can be formed from at least a cationic silicon-containing biomedical device-forming monomer. In another embodiment, a silicon-containing biomedical device for use herein can be formed from at least a fluorinated silicon-containing biomedical device-forming monomer.

Such material have been used in the formation of fluorosilicon hydrogels to reduce the accumulation of deposits on contact lenses made therefrom, as disclosed in, for example, U.S. Pat. Nos. 4,954,587; 5,0110,141 and 5,079,319. The use of silicon-containing biomedical device-forming monomers having certain fluorinated side groups, i.e., —$(CF_2)$—H can also be used herein, such as those disclosed in, e.g., U.S. Pat. Nos. 5,321,108 and 5,387,662.

The monomer mixture employed in the method of the present invention to obtain the silicon-containing biomedical devices can contain one or more comonomers in addition to the one or more silicon-containing biomedical device-forming monomers. Examples of suitable comonomers include the hydrophilic comonomers, and hydrophobic monomers discussed above.

The monomer mixture can also include a crosslinking monomer (a crosslinking monomer or crosslinker being defined as a monomer having multiple polymerizable functionalities). In the case where the silicon-containing biomedical device-forming monomer is a prepolymer end-capped at both ends with a polymerizable radical, these prepolymers can function as a crosslinker. Optionally, other supplemental crosslinking monomer may be added to the initial monomeric mixture. Representative crosslinking monomers include: divinylbenzene, allyl methacrylate, ethyleneglycol dimethacrylate, tetraethyleneglycol dimethacrylate, polyethyleneglycol dimethacrylate, vinyl carbonate derivatives of the glycol dimethacrylates, and methacryloxyethyl vinylcarbonate. When a supplemental crosslinking agent is employed, this monomeric material may be included in the monomer mixture at 0.1 to 20 weight percent, more preferably at 0.2 to 10 weight percent.

The boric acid ester present in the monomer mixture is a boric acid ester of a $C_1$ to $C_8$ monohydric alcohol and is used in the method of the present invention as a water-displaceable diluent/solubilizer/solvent/viscosity modifier. The boric acid esters are prepared by procedures analogous to those that are known in the art, such as the monohydric alcohol boric acid esters prepared in U.S. Pat. Nos. 6,998,465, and 8,967,799, the contents of which are incorporated by reference herein. For example, the boric acid esters of a $C_1$ to $C_8$ monohydric alcohol used in the method of the present invention can be obtained by reacting boric acid or anhydrous boric acid with a $C_1$ to $C_8$ monohydric alcohol and removing the water formed by the reaction by normal procedures such as by vacuum distillation. The boric acid compound and monohydric alcohol are mixed together in an amount ranging from about 1 mole equivalent of boric acid and from about 3.0 to about 6.0 mole equivalents of monohydric alcohol. The reaction of boric acid with the monohydric alcohol is carried out at a temperature and for a period of time sufficient to form the ester. Typical reaction temperatures are usually found within the range of from about 15° C. to about 100° C. At these temperatures, reaction times will ordinarily range from about 1 to about 24 hours. In general, the reaction is continued until the water content of the ester is less than about 2%, by weight. Some of the boric acid esters such as, for example, tri(isopropyl)borate, tri (methyl) borate, tri(t-butyl) borate and tri(n-butyl) borate are commercially available from sources as Aldrich. Alternatively these boric acid esters can be prepared by methods well known in the art.

In one embodiment, examples of suitable monohydric alcohols would include a $C_1$ to $C_8$ straight or branched chain monohydric alcohols, $C_5$ to $C_8$ cycloalkyl monohydric alcohols, $C_5$ to $C_8$ aromatic monohydric alcohols and mixtures of any of the above. Useful monohydric alcohols would include, but not be limited to, methanol, ethanol, propanol, n-propanol, iso-propanol, n-butanol, t-butanol, isobutanol, 2-ethylhexanol, 2-methylcyclohexanol, 2-methyl-1-propanol, n-pentanol, 2-pentanol, 3-pentanol, 2-methyl-1-butanol, 3-methyl-1-butanol, 2-methyl-2-butanol, 3-methyl-2-butanol, 3,7-dimethyl-3-octanol, 2,2-dimethyl-1-propanol, 1-hexanol, 1-octanol, 2-octanol, cyclohexanol, cyclopentanol, benzyl alcohol, and the like and mixtures thereof.

Representative examples of suitable boric acid ester for use herein would therefore include, but not be limited to, trimethyl borate, triethyl borate, tri-n-propyl borate, triisopropyl borate, tri-n-butyl borate, tri-tert-butyl borate and the like and mixtures thereof In general, the boric acid ester of a $C_1$ to $C_8$ monohydric alcohol is present in the monomer mixture in an amount of about 5 to about 50 percent by weight, based on the total weight of the monomer mixture. In one embodiment, the boric acid ester of a $C_1$ to $C_8$ monohydric alcohol is present in the monomer mixture in an amount of about 15 to about 30 percent by weight, based on the total weight of the monomer mixture.

If desired, the monomer mix can also contain the corresponding monohydric alcohol used to form the boric acid ester as an additional diluent in the monomer mix. Examples of such monohydric alcohols include those discussed above.

The monomeric mixture may further contain, as necessary and within limits not to impair the purpose and effect of the present invention, various additives such as an antioxidant, coloring agent, ultraviolet absorber, lubricant internal wetting agents, toughening agents and the like and other constituents as is well known in the art.

Generally, contact lenses can be obtained by curing the monomer mixture under conditions sufficient to polymerize the monomer mixture to produce a water extractable silicon-containing biomedical device. Various processes are known for curing a monomeric mixture in the production of contact lenses including, by way of example, spincasting and static casting. For example, spincasting methods involve charging the monomer mixture in an open faced mold having a concave bottom surface, i.e., a one-piece mold, and spinning the mold in a controlled manner while exposing the monomer mixture to light, such as UV light. Static casting methods involve charging the monomer mixture between two mold sections, one mold section shaped to form the anterior lens surface and the other mold section shaped to form the posterior lens surface, and curing the monomer mixture while retained in the mold assembly to form a lens, for example, by free radical polymerization of the mixture. Spincasting methods are disclosed in U.S. Pat. Nos. 3,408, 429 and 3,660,545, and static casting methods are disclosed in U.S. Pat. Nos. 4,113,224, 4,197,266, and 5,271,875. Additionally, the monomer mixtures may be cast in the shape of rods or buttons, which are then lathe cut into a desired lens shape.

Polymerization may be facilitated by exposing the mixture to heat and/or radiation, such as ultraviolet light, visible light, or high energy radiation. A polymerization initiator may be included in the mixture to facilitate the polymerization step. Representative examples of free radical thermal polymerization initiators include organic peroxides such as acetyl peroxide, lauroyl peroxide, decanoyl peroxide, stearoyl peroxide, benzoyl peroxide, tertiarylbutyl peroxypivalate, peroxydicarbonate, and the like and azo compounds such as 2,2'-azobisisobutyronitrile (AIBN), 1,1'-azobis(cyclohexanecarbonitrile), 4,4'-azobis(4-cyanovaletic acid), and the like. Representative UV initiators are those known in the art and include benzoin methyl ether, benzoin ethyl ether, Darocure 1173, 1164, 2273, 1116, 2959, 3331 (EM Industries) and Irgacure 651 and 184 (BASF), and the like. Representative examples of visible light initiators include phosphine oxides such as Irgacure 819, Darocure TPO (BASF), Lucirin TPO, Lucirin TPO-L (BASF), etc. Generally, the initiator will be employed in the mixture at a concentration of about 0.01 to about 5 percent by weight of the total monomer mixture.

Generally, polymerization under ultra-violet (UV) or Visible light ('blue light') curing polymerization conditions can be carried out for about 15 minutes to about 60 minutes and under an inert atmosphere of, for example, nitrogen or argon. Polymerization under thermal curing conditions generally require higher temperatures, e.g., about 40 to about 120° C. for a time period of about 10 to about 72 hours.

Following casting, the polymerization product (silicon-containing biomedical device) is dry released from the mold. In the case where the mold is a two-part mold assembly, including a posterior mold half and an anterior mold half, dry release is carried out when one of the mold halves is removed, i.e., de-capped, with the cast polymerization product remaining adhered to the other mold half. In many processes, it is desired that the polymerization product remains with the anterior mold half. In general, a dry release process involves releasing the polymerization product from the mold half in a dry state and without adding aqueous media. While not wishing to be bound by theory, it is believed that the boric acid ester of a $C_1$ to $C_8$ monohydric alcohol cross-links with the polymerization product during curing such that the polymerization product possesses a sufficient hardness to allow it to be dry released from the mold. One skilled in the art would readily appreciate that the term "sufficient hardness" means that the resulting polymerization product is not too soft so that it tears during the dry release process e.g., when being removed from mold with mechanical grippers) or is too brittle such that it shatters or breaks upon being subjected to the mechanical forces encountered during the dry release process.

In one embodiment, the polymerization product can be dry released by simply removing the polymerization product from the mold in a dry state. In another embodiment, dry release is accomplished by way of mechanical actions in which the polymerization product is removed mechanically from the molds using mechanical grippers such as tweezers, taking a precaution of not to tear the polymerization product. In the event that mechanical removal cannot be carried out, the mold half containing the polymerization product is mechanically deformed to forcibly dry release it.

Once the biomedical devices such as contact lenses are dry released, they can then be subjected to optional machining operations. For example, the machining operation could include one of the following three lathing (machining) operations of the lenses:

1. A monomer mix is cast and cured in a long cylindrical mold, the resulting rod (hard plastic at this point) is removed from the mold, cut into smaller discs and subsequently lathed on both sides to form a lens. The resulting lens is then extracted and hydrated.

2. A monomer mix is cast into a short cylindrical mold to form a hard plastic button (disc-like) which is removed from the mold and lathed on both sides to form a lens. The resulting lens is then extracted and hydrated. This process avoids the cutting step.

3. A monomer mix is cast into a single part, half mold, i.e., a one piece mold (with curvature on one side only). The mold may or may not have a lid to cover the flat side. The monomer mix is then cured and the dome-shaped hard part is removed from the mold and machined. Lathing is confined to one side only to generate the concave half of the lens. The lens is then extracted and hydrated.

Other optional machining steps may include buffing or polishing a lens edge and/or surface. Generally, such machining processes may be performed before or after the product is released from a mold part, e.g., the lens is dry released from the mold by employing vacuum tweezers to lift the lens from the mold, after which the lens is transferred by means of mechanical tweezers to a second set of vacuum tweezers and placed against a rotating surface to smooth the surface or edges. The lens may then be turned over in order to machine the other side of the lens.

If desired, once the polymerization product is dry released and optionally lathed, it can be extracted with a suitable solvent in which the crosslinks of the boric acid ester of a $C_1$ to $C_8$ monohydric alcohol are broken and the boric acid ester is displaced from the polymerization product to provide a water extractable silicon-containing biomedical device. A suitable solvent includes a polar solvent. Useful polar solvents include water, alcohols, esters, hydroxy and glycol esters, polyols and ketones, and mixtures thereof.

Suitable alcohols for extraction include, but are not limited to, straight or branched chain $C_1$ to $C_5$ alcohols, such as methanol, ethanol, n-propanol, iso-propanol, mixtures of propanol isomers, n-butanol, sec-butanol, tert-butanol, iso-butanol, mixtures of butanol isomers 2-methyl-1-butanol, n-pentanol, mixtures of pentanol isomers and amyl alcohol (mixture of isomers), and mixtures thereof.

Suitable esters for extraction include, but are not limited to, methyl acetate, ethyl acetate, n-propyl acetate, iso-propyl acetate, n-butyl acetate, iso-butyl acetate, sec-butyl acetate, amyl acetate (mixture of isomers), methylamyl acetate, 2-ethylhexyl acetate and iso-butyl isobutyrate, and mixtures thereof.

Suitable hydroxy and glycol esters for extraction include, but are not limited to, methyl glycol acetate, ethyl glycol acetate, butyl glycol acetate, ethyl diglycol acetate, butyl diglycol acetate, ethyl lactate, n-butyl lactate, 3-methoxy-n-butyl acetate, ethylene glycol diacetate, glycolic acid-n-butyl ester, 2-methylpropanoic acid-2,2,4-trimethyl-3-hydroxypentyl ester, methyl glycol, ethyl glycol, iso-propyl glycol, 3-methoxybutanol, butyl glycol, iso-butyl glycol, methyl diglycol, ethyl diglycol, butyl diglycol, iso-butyl diglycol, diethylene glycol, dipropylene glycol, ethylene glycol monohexyl ether and diethylene glycol monohexyl ether, and mixtures thereof Suitable polyols for extraction include, but are not limited to, ethylene glycol, propylene glycol, 1,3-butylene glycol, 1,4-butylene glycol, hexylene glycol, diethylene glycol, triethylene glycol and dipropylene glycol, and mixtures thereof.

Suitable ketones for extraction include, but are not limited to, iso-butyl heptyl ketone, cyclohexanone, methyl cyclohexanone, methyl iso-butenyl ketone, pent-ozone, acetyl acetone, diacetone alcohol, iso-phorone, methyl butyl ketone, ethyl propyl ketone, methyl iso-butyl ketone, methyl amyl ketone, methyl iso-amyl ketone, ethyl butyl ketone, ethyl amyl ketone, methyl hexyl ketone, diisopropyl ketone, diisobutyl ketone, acetone, methyl ethyl ketone, methyl propyl ketone and diethyl ketone, and mixtures thereof.

The extracted polymerization product is then hydrated with water or an aqueous solvent, e.g., 50% V/V isopropyl alcohol, to form a hydrogel as discussed above.

The lens may then be transferred to individual lens packages containing a buffered saline solution. The saline solution may be added to the package either before or after transfer of the lens. Appropriate packaging designs and materials are known in the art. A plastic package is releasably sealed with a film. Suitable sealing films are known in the art and include foils, polymer films and mixtures thereof. The sealed packages containing the lenses are then sterilized to ensure a sterile product. Suitable sterilization means and conditions are known in the art and include, for example, autoclaving.

As one skilled in the art will readily appreciate other steps may be included in the molding and packaging process described above. Such other steps can include, for example, coating the formed lens, surface treating the lens during formation (e.g., via mold transfer), inspecting the lens, discarding defective lenses, cleaning the mold halves, reusing the mold halves, and the like and combinations thereof.

The following examples are provided to enable one skilled in the art to practice the invention and are merely illustrative of the invention. The examples should not be read as limiting the scope of the invention as defined in the claims.

Various polymerization products were formed as discussed below and characterized by standard testing procedures such as:

Contact Angle: Captive bubble contact angle (CBCA) data was collected on a First Ten Angstroms FTA-1000 prop Shape Instrument. All samples were rinsed in HPLC grade water prior to analysis in order to remove components of the packaging solution from the sample surface. Prior to data collection the surface tension of the water used for all experiments was measured using the pendant drop method. In order for the water to qualify as appropriate for use, a surface tension value of 70-72 dynes/cm was expected. All lens samples were placed onto a curved sample holder and submerged into a quartz cell filled with HPLC grade water. Advancing and receding captive bubble contact angles were collected for each sample. The advancing contact angle is defined as the angle measured in water as the air bubble is retracting from the lens surface (water is advancing across the surface). All captive bubble data was collected using a high speed digital camera focused onto the sample/air bubble interface. The contact angle was calculated at the digital frame just prior to contact line movement across the sample/air bubble interface. The receding contact angle is defined as the angle measured in water as the air bubble is expanding across the sample surface (water is receding from the surface).

Modulus (g/mm$^2$) was measured per ASTM 1708 employing an Instron (Model 4502) instrument where the film sample was immersed in borate buffered saline; an appropriate size of the film sample was gauge length 22 mm and width 4.75 mm, where the sample further has ends forming a dogbone shape to accommodate gripping of the sample with clamps of the Instron instrument, and a thickness of 100±50 microns.

Water Content was measured by individually placing the lens on a piece of premoistened Whatman #1 filter paper. The surface moisture is removed by lightly smoothing a second piece of premoistened Whatman #1 filter paper over the lens. After checking the accuracy of the balance with two known weights, the lens is placed in a tared weigh boat. The wet weight is recorded to the nearest 0.1 mg and the lens transferred to the lens holder, concave side up (this allows the lens identity to be maintained to match wet and dry weights). After the lens holders are full, they are placed on a spindle with a plastic spacer between them and placed in a glass jar approximately ½ full of desiccant. The jar is capped and the lid tightened, then loosened slightly to prevent pressure buildup. The jar with lenses is placed in a 500-650 watt microwave oven along with a 400 ml beaker containing at least 200 ml of distilled water with boiling beads to keep the jar from becoming overheated. The jar is microwaved at 500-650 watts for 10 minutes; the start time and date are recorded on the paperwork. When the cycle finishes, the jar is removed from the microwave and allowed to cool on the bench for 30 minutes; time out and date are also recorded. When cool, the lenses are individually weighed and their dry weights recorded to the nearest 0.1 mg, matching the dry weights to the corresponding wet weight. The water content is expressed as % water according to the following formula:

$$\text{Water Content (\%)} = \frac{\text{Wet Weight} - \text{Dry Weight}}{\text{WetWeight}} \times 100$$

Sagittal depth (SAG) as measured on a Deltronic Comparator.

The Ma2D37 concentration in Tables 2, 4, 6, 8, 10, 12, 14, and 16 was determined from a mass spectrometry method as follows:

HR/AM LC-MS Instrument Conditions

Ultra High Performance Liquid Chromatography (UHPLC or LC) separation was combined with High Resolution Accurate Mass (HR/AM) Mass Spectrometry (aka HR/AM LC-MS) for the analysis of the silicone polymer materials. The instrument was configured such that the eluent from the UHPLC column passed directly into the ionization source of the mass spectrometer. The UHPLC separation was performed using an Ultimate 3000 RSLC instrument (Thermo-Dionex, Sunnyvale, Calif.). The separations were performed using an Eclipse XDB C-18 UHPLC column (1.8 μ, 150 mm×2.1 mm), obtained from Agilent Technologies (Santa Clara, Calif.) held at a constant temperature of 50° C. The injection volume for all analyses was 1.0 μL. The reverse phase mobile phases (solvents) for the final silicone polymer screening methodology were as follows: A phase: 0.001 M ammonium formate (unbuffered); B phase: isopropanol: THF (1:1 mixture by volume). The reverse phase gradient conditions and flow rate are included in the table below.

| Time | % A | % B | Flow Rate mL/min |
|---|---|---|---|
| 0.0 | 50 | 50 | 0.2 |
| 45.0 | 5 | 95 | 0.2 |
| 50.0 | 0 | 100 | 0.2 |
| 53.0 | 0 | 100 | 0.2 |

High resolution/accurate mass data was collected using an LTQ Orbitrap XL (Thermo Scientific, Bremen, Germany), equipped with an Ion-Max source using a heated electrospray probe (HEM). All data was collected with the orbitrap resolution setting at 60,000, with a mass range of 200-4000 Da. The electrospray source conditions for LC-MS analysis were: source voltage 4.5 kV, capillary voltage 35 V, tube lens voltage 140V, skimmer offset voltage 0 V, vaporizer temperature 300 C, capillary temperature 250 C, sheath gas flow 50, auxiliary gas flow 10, sweep gas flow 0.

Normalized Relative Purity Data Processing

After data was collected as total-ion-chromatograms (TIC), the data files were processed to evaluate normalized relative purity. Extracted ion peaks from each individual end-group component distribution were integrated. Extracted ion chromatograms were prepared using the first three isotopes from the proton, ammonium, and sodium adduct mass spectrometry peak accurate mass/charge (m/z) values for oligomers up to 3000 Da. Peak areas from an individual component distribution were summed to give one area per end-group component. Areas of all components are summed to give a "total area". The relative area percent was calculated using the following equation:

Area %=(individual component combined area/Total Area)×100

For every data set collected, a reference lot of Ma2D37 was also analyzed for comparison. The relative purity of each sample was normalized to the normalized purity of the reference to give Normalized Relative Purity. Note: Normalized Relative Purity Data was used to make relative comparisons and Area % does not equal necessarily equal Weight %.

EXAMPLE 1

Synthesis for 100% methacrylic anhydride.

All glassware was dried in an oven prior to use. A three-neck round bottom flask was assembled with a condenser set to 10° C., purged with $N_2$ and placed in a 35° C. oil bath. The PDMS of structure (1) having 37 units on average (0.015 moles), 4-dimethylaminopyridine (DMAP) (0.001506 moles), 4-Methyl-2,6-di-tert-butyl phenol (BHT) (0.000118 moles), and dichloromethane (DCM) (150 mL) were added to the round bottom flask. Triethylamine (0.09 moles) was added to the round bottom flask. Next, methacrylic anhydride (0.067 moles) was added with 60 mL of DCM and stirred overnight. The next day heat was removed; 150 mL $H_2O$ and 0.430 mL aliquat 336 (tricaprylylmethylammonium chloride) (Sigma Aldrich) were added and stirred overnight. The following day the organic layer was isolated and washed separately with the following aqueous solutions: 10% HCl, 10% sodium bicarbonate, and 5% NaCl. The organic layer was added to a separatory funnel and 250 mL of each aqueous phase was used per wash. Each aqueous phase was repeated twice. The organic layer was stirred in DMAP and triethylamine overnight. The organic layer was washed with the aqueous phases a second time, and dried in ~50 wt. % magnesium sulfate and sodium sulfate. The resulting Ma2D37 is of the following structure (2).

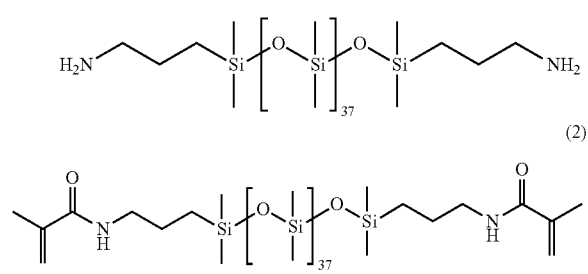

EXAMPLE 2

Synthesis for 95% methacrylic anhydride feed (95:5) in which 5% of the amino termini from the PDMS will be capped with acetamide end groups, and the remaining 95% will have methacrylamide end groups.

All glassware was dried in an oven prior to use. A three-neck round bottom flask was assembled with a condenser set to 10° C., purged with $N_2$ and placed in a 35° C. oil bath. The PDMS (0.100665 moles), DMAP (0.009822 moles), BHT (0.000862 moles), and DCM were added to the round bottom flask. Triethylamine (0.43 moles) was added to the roundbottom flask, 150 mL of DCM was added to the addition funnel along with acetic anhydride (0.010067 moles). The acetic anhydride (0.01005 moles) was added dropwise and slowly to the rapidly stirring reaction. Once the addition was completed the reaction was stirred overnight. The following day methacrylic anhydride (0.401068 moles) was added with 150 mL of DCM and stirred overnight. The next day heat was removed; 400 mL $H_2O$ and 2 mL aliquat 336 (Sigma Aldrich) were added and stirred overnight. The following day the organic layer was isolated and washed with 10% aq. HCl, 10% aq. sodium bicarbonate, and 5% aq. NaCl. For the washing steps, the organic layer was divided amongst two separatory funnels and 250 mL of each aqueous phase was used per wash. Each aqueous phase was repeated twice. The organic layer was stirred in DMAP and triethylamine overnight. The organic layer was washed with the aqueous phases a second time, and dried in ~50 wt % magnesium sulfate and sodium sulfate. The partially capped Ma2D37 was isolated via filtration and solvent removed with a Rotary Evaporator (i.e., rotovap) to provide the following distribution of products:

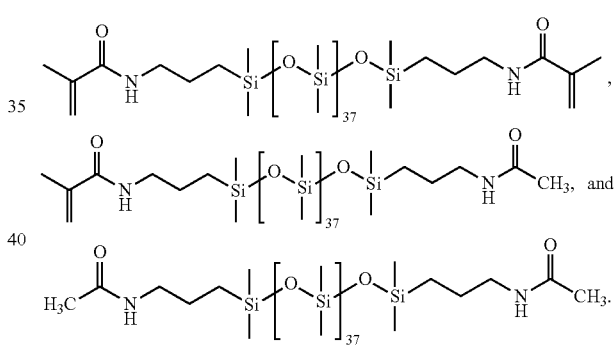

EXAMPLE 3

Synthesis for 93% methacrylic anhydride feed (93:7).

All glassware was dried in an oven prior to use. A three-neck round bottom flask was assembled with a condenser set to 10° C., purged with $N_2$ and placed in a 35° C. oil bath. The PDMS (0.100267 moles), DMAP (0.010027 moles), BHT (0.001003 moles), and DCM (450 mL) were added to the round bottom flask. Triethylamine (0.441175 moles) was added to the round bottom flask. 150 mL of DCM was added to the addition funnel along with the acetic anhydride (0.014037 moles). Acetic anhydride was added (0.014037 moles) dropwise and slowly to the rapidly stirring reaction. Once the addition was completed the reaction was stirred overnight. The following day methacrylic anhydride (0.401068 moles) was added with 150 mL of DCM from an addition funnel and stirred overnight. The next day heat was removed; 400 mL $H_2O$ and 2 mL aliquat 336 (Sigma Aldrich) were added and stirred overnight. The following day the organic layer was isolated and washed with 10% aq. HCl, 10% aq. sodium bicarbonate, and 5% aq. NaCl. The organic layer was divided amongst two separatory funnels and 250 mL of each aqueous phase was used per wash, Each aqueous phase was repeated twice. The organic layer was stirred in DMAP and triethylamine overnight. The organic layer was washed with the aqueous phases a second time, and dried with ~50 wt % magnesium sulfate and sodium sulfate. The partially capped Ma2D37 was isolated via filtration and solvent removed with a rotovap to provide the following distribution of products.

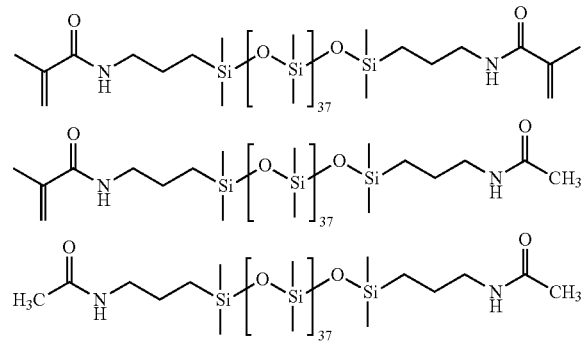

EXAMPLE 4

Synthesis for 90% methacrylic anhydride feed (90:10).

A three-neck round bottom flask and an addition funnel were dried in an oven prior to use. The flask was assembled with a condenser set to 10° C., placed in a 35° C. oil bath and the apparatus was purged with $N_2$. The PDMS (0.006684 moles), DMAP (0.000608 moles), BHT (0.00007 moles) and 75 mL of DCM were added to the round bottom flask. Triethylamine (0.02941 moles) was added to the round bottom flask, and the acetic anhydride was transferred to the addition funnel (0.001337 moles). This was added dropwise and stirred overnight. Methacrylic anhydride (0.02736 moles) was added dropwise and was stirred overnight. The following day 35 mL of $H_2O$ and 215 μL of aliquat 336 (Sigma Aldrich) were added and stirred overnight. The product was washed with 10% aq. HCl (125 mL×2), 10% aq. sodium bicarbonate (125 mL×2), and 5% aq. NaCl (125 mL×2). The organic layer was stirred in triethylamine and DMAP overnight. The organic layer was washed again with the aqueous phases mentioned previously. The organic phase was dried with sodium sulfate and magnesium sulfate overnight (~50 wt %), and the next day the solvent was removed with a rotovap to provide the following distribution of products:

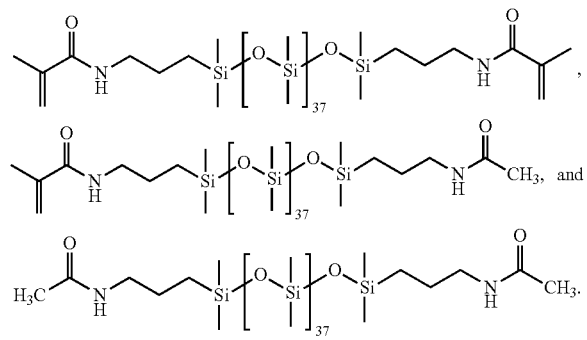

EXAMPLE 5

All glassware was dried in an oven prior to use. PDMS (0.015039 moles), DMAP (0.0015039 moles), BHT (0.000073), 160 mL of DCM and triethylamine (0.064516 moles) were added to a three-neck round bottom flask. The flask was purged with $N_2$, and cooled in an ice bath below 10° C. Next, 60 mL of DCM was added to the addition funnel, followed by the acetyl chloride. The acetyl chloride was added dropwise (0.001504 moles). After 3-4 hours, an aliquot of the solution was removed, the DCM removed via rotovap, and analyzed via $^1$H NMR spectroscopy. The spectrum indicated ~4.9% of the acetyl chloride had reacted. Next, 60 mL of DCM was added to the addition funnel, and methacryloyl chloride (0.057147 moles). This was added dropwise, and once addition was completed the reaction was left to stir overnight and equilibrate to room temperature. An aliquot of the solution was taken, concentrated via rotovap and analyzed via $^1$H NMR spectroscopy. The spectrum showed full conversion of the primary amine to amide. The product was extracted with 1N aq. HCl (200 mL 3×) and no emulsion occurred. The organic layer was extracted with 1N aq. Na.OH (200 mL 3×), and distilled water (200 mL 3×). The organic layer was dried with sodium sulfate and magnesium sulfate. The product was concentrated via rotovap, and analyzed via $^1$H NMR spectroscopy. The spectrum indicated the product still contained methacrylic acid, since there were additional peaks from ~5-6 ppm which are from the methacrylate functional group. The product was diluted in DCM, and extracted with 1N aq. HCl (3×100 mL), 1N aq. NaOH (3×100 mL), and distilled water (3×100 mL). The organic layer was dried with sodium sulfate and magnesium sulfate. The resulting Ma2D37 was then concentrated via rotovap.

EXAMPLE 6

A 500mL-3neck Morton flask equipped with a large magnetic stir bar, $N_2$ blanket, dimroth condenser (set to 0° C.) and rubber/teflon stoppers at any openings was set up. All glassware was flame dried. The dry reaction flask was charged with IEM (0.0503 moles) and DMAP (0.000033 moles) dissolved in anhydrous dichloromethane using the addition funnel, PDMS (0.0167 moles) dissolved in anhydrous dichloromethane was added dropwise over a 3 hour period. Once addition was finished allowed reaction to stir overnight at room temperature, reaction was followed via FT-IR. When no NCO peak was observed in FT-IR, solvent was removed under reduced pressure.

EXAMPLE 7

Set up a 500mL-3neck Morton flask equipped with a large magnetic stir bar, $N_2$ blanket, dimroth condenser (set to 0° C.) and rubber/teflon stoppers at any openings. All glassware was flame dried. The dry reaction flask was charged with PDMS (0.0168 moles)/DMAP (0.000033 moles) dissolved in anhydrous dichloromethane using the addition funnel. Octyl isocyanate (0.000833 moles) dissolved in anhydrous dichloromethane was added dropwise. The following day, additional DMAP (0.001465 moles), BHT (0.000118 moles), triethylamine were (0.066007 moles) added to the flask. The reaction flask was added to an oil bath set to 35° C. Methacrylic anhydride (0.060042 moles) was added to the addition funnel containing 25 mL of anhydrous dichloromethane. This was added dropwise. The following day, heat was removed and 75 mL of distilled $H_2$) and 430 μL of aliquat 336 were added. This was stirred overnight. The product was washed with 10% HCl (250 mL×2), 10% aq. sodium bicarbonate (250 mL×2), and 5% aq. NaCl (250 mL×2). The organic phase was stirred in 5 mL of triethylamine and DMAP overnight. The following day the product was washed with 10% aq. HCl (250 mL×2), 10% aq. sodium bicarbonate (250 mL×2), and 5% aq. NaCl (250 mL×2). The organic layer was then dried with sodium sulfate and magnesium sulfate overnight. The solvent was removed via rotovap, and final traces of drying agent were removed via Millipore filtration.

In the examples below, the following abbreviations are used.

TRIS: 3-[Tris(trimethylsiloxy)silyl]propyl methacrylate
DMA: N,N-dimethylacrylamide.
HEMA: 2-hydroxyethyl methacrylate.
NVP: N-vinyl-2-pyrrolidone.
M1EDS6: a compound having the structure and available from Gelest:

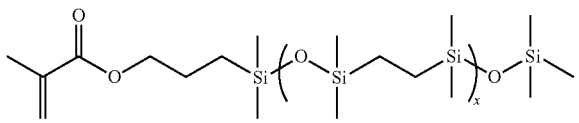

where x is 6.
BPA-1: 2-(4-Benzoyl-3-hydroxyphenoxy) ethyl acrylate.
CIX-4: a cross-linking compound having the structure:

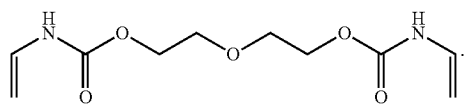 [SMILES: C=CNC(=O)OCCOCCOC(=O)NC=C]

Tint: Reactive blue tint available from Arran.
Irgacure 819: a photoinitiator for free radical polymerization available from Sigma Aldrich.

EXAMPLE 8

Preparation of a contact lens.
A monomer mixture was made by mixing the following components, at amounts per weight, together with the polysiloxane prepolymer (Ma2D37) obtained in Example 1, as set forth in Table 1 below.

TABLE 1

| Ingredient | Parts by Weight |
| --- | --- |
| Ma2D37 of Example 1 | 7.4 |
| TRIS | 36.52 |

TABLE 1-continued

| Ingredient | Parts by Weight |
| --- | --- |
| NVP | 32.34 |
| HEMA | 4.97 |
| DMA | 4.97 |
| M1EDS6 | 13.29 |
| Monomer Mix (total) | 99.49 |
| Hexanol | 7.5 |
| Irgacure 819 | 0.5 |
| Tint | 0.02 |

The resultant monomeric mixture was cast into contact lenses by introducing the monomer mixture to a polypropylene mold assembly. Then, the mold assembly and monomer mixture were polymerized at 421 nm for 25 minutes at 5 mW/cm$^2$ to form a contact lens. The resultant contact lenses were released from the mold assembly. The contact lenses were extracted using the following process: 10 minutes in 50% isopropyl alcohol, 30 minutes in 100% isopropyl alcohol, 10 minutes in 50% isopropyl alcohol, 10 minutes in distilled water, and 10 minutes distilled water.

Next, the lens obtained were characterized by standard testing procedures as set forth below in Table 2. The Ma2D37s used in the lens formulations set forth in Table 2 were synthesized using methacrylic anhydride.

TABLE 2

Methacrylic anhydride synthesized Ma2D37 and Lens Property Data (100:0)

| Example | Ma2D37 Lot | Ma2D37 Concentration | Lens Modulus | Lens CBCA | Lens Diameter | Lens Sag | Lens WC % |
| --- | --- | --- | --- | --- | --- | --- | --- |
| 1 | 4043-80 | 97.6 | 80 | 34 | 14.199 | 3.992 | 46.7 |
| 1 | 4043-80 | 97.6 | 73 | 31 | 14.329 | 3.874 | 45.9 |
| 1 | 4043-80 | 97.6 | 75 | 36 | 14.190 | 3.909 | 46.0 |
| 1 | 4057-72 | 85.9 | 67 | 39 | 14.418 | 3.853 | 46.9 |
| 1 | 8H-33848 | 91.5 | 77 | 36 | 14.185 | 3.915 | 46.4 |
| 1 | 8H-33848 | 91.5 | 85 | 34 | N/A | N/A | N/A |
| 1 | 8H-33848 | 91.5 | 82 | N/S | N/S | N/S | N/S |
| 1 | 8H-33848 | 91.5 | N/S | N/S | 14.243 | 3.913 | 46.9 |
| 1 | 8H-33848 | 91.5 | 72 | 34 | 14.182 | 3.931 | 46.2 |
| 1 | 9B-34933 | 84.5 | 75 | 47 | 14.222 | 3.970 | 46.3 |
| 1 | 9B-34933 | 84.5 | 74 | 35 | 14.382 | 4.086 | 48.0 |

EXAMPLES 9-20

Preparation of a contact lens.
A monomer mixture was made by mixing the following components, in amounts of parts by weight, together with the polysiloxane prepolymer obtained in Example 2, as set forth below in Table 3.

TABLE 3

| Ex. | TRIS | Ma2D37 (95:5) | NVP | HEMA | DMA | M1EDS6 | BPA-1 | CIX-4 | Monomer Mix (total) | Irgacure 819 | Visibility Tint | Hexanol |
| --- | --- | --- | --- | --- | --- | --- | --- | --- | --- | --- | --- | --- |
| 9 | 36.52 | 7.4 | 32.34 | 4.97 | 4.97 | 13.29 | 0 | 0.0 | 99.49 | 0.5 | 0.02 | 7.5 |
| 10 | 36.52 | 7.4 | 32.34 | 4.97 | 4.97 | 13.29 | 0 | 0.1 | 99.59 | 0.5 | 0.02 | 7.5 |
| 11 | 36.52 | 7.4 | 32.34 | 4.97 | 4.97 | 13.29 | 0 | 0.2 | 99.69 | 0.5 | 0.02 | 7.5 |
| 12 | 36.52 | 7.4 | 32.34 | 4.97 | 4.97 | 13.29 | 0 | 0.3 | 99.79 | 0.5 | 0.02 | 7.5 |
| 13 | 36.52 | 7.4 | 32.34 | 4.97 | 4.97 | 13.29 | 0 | 0.4 | 99.89 | 0.5 | 0.02 | 7.5 |
| 14 | 36.52 | 7.4 | 32.34 | 4.97 | 4.97 | 13.29 | 0 | 0.5 | 99.99 | 0.5 | 0.02 | 7.5 |
| 15 | 36.52 | 7.4 | 32.34 | 4.97 | 4.97 | 13.29 | 0 | 0.6 | 100.09 | 0.5 | 0.02 | 7.5 |
| 16 | 30 | 7.4 | 38 | 4 | 4 | 13.3 | 1 | 0.0 | 97.70 | 0.5 | 0.02 | 7.5 |

TABLE 3-continued

| Ex. | TRIS | Ma2D37 (95:5) | NVP | HEMA | DMA | M1EDS6 | BPA-1 | CIX-4 | Monomer Mix (total) | Irgacure 819 | Visibility Tint | Hexanol |
|---|---|---|---|---|---|---|---|---|---|---|---|---|
| 17 | 30 | 7.4 | 38 | 4 | 4 | 13.3 | 1 | 0.1 | 97.80 | 0.5 | 0.02 | 7.5 |
| 18 | 30 | 7.4 | 38 | 4 | 4 | 13.3 | 1 | 0.2 | 97.90 | 0.5 | 0.02 | 7.5 |
| 19 | 30 | 7.4 | 38 | 4 | 4 | 13.3 | 1 | 0.4 | 98.10 | 0.5 | 0.02 | 7.5 |
| 20 | 30 | 7.4 | 38 | 4 | 4 | 13.3 | 1 | 0.6 | 98.30 | 0.5 | 0.02 | 7.5 |

The resultant monomeric mixture was cast into contact lenses by introducing the monomer mixture to a polypropylene mold assembly. Then, the mold assembly and monomer mixture were polymerized at 421 nm for 25 minutes at 5 mW/cm$^2$ to form a contact lens. The resultant contact lenses were released from the mold assembly. The contact lenses were extracted using the following process: 10 minutes in 50% isopropyl alcohol, 30 minutes in 100% isopropyl alcohol, 10 minutes in 50% isopropyl alcohol, 10 minutes in distilled water, and 10 minutes distilled water.

Next, the lens obtained were characterized by standard testing procedures as set forth below in Table 4. The Ma2D37s used in the lens formulations set forth in Table 4 were synthesized using methacrylic anhydride and acetic anhydride to form a dead end (i.e., non-reactive end) of the polymer.

TABLE 4

Methacrylic anhydride synthesized Ma2D37 and Lens Property Data (95:5)

| Example | Ma2D37 Lot | Ma2D37 Concentration | Lens Modulus | Lens CBCA | Lens Diameter | Lens Sag | Lens WC % |
|---|---|---|---|---|---|---|---|
| 9 | 4057-201 | 82.1 | 56 | 51 | 14.489 | 4.149 | 49.9 |
| 9 | 4057-201 | 82.1 | 60 | 51 | 14.497 | 4.117 | 49 |
| 9 | 4057-204 | 88.2 | 63 | 35 | 14.500 | 4.109 | 49.2 |
| 9 | 4057-204 | 88.2 | 61 | 36 | 14.500 | 4.239 | 49.1 |
| 9 | 8H-33753 | 78.4 | 72 | 32 | 14.145 | 3.919 | 46.7 |
| 9 | 8H-33753 | 78.4 | 72 | 34 | 14.260 | 3.962 | 47.1 |
| 9 | 8H-33753 | 78.4 | 66 | 37 | 14.275 | 3.991 | 48.4 |
| 9 | 8H-33753 | 78.4 | 66 | 39 | 14.296 | 3.962 | 49.1 |
| 9 | 8H-33753 | 78.4 | 66 | 34 | 14.249 | 3.875 | 48.7 |
| 9 | 8H-33753 | 78.4 | 55 | 33 | 14.492 | 4.081 | 50.6 |
| 9 | 8H-33753 | 78.4 | 56 | 34 | 14.488 | 4.086 | 50.4 |
| 9 | 9A-34895 | 74.3 | 66 | 67 | 14.263 | 4.094 | 47.4 |
| 9 | 9A-34895 | 74.3 | 62 | 33 | 14.420 | 4.026 | 49.7 |
| 9 | 9A-34895 | 74.3 | 61 | 33 | 14.410 | 4.023 | 49.4 |
| 9 | 9A-34894 | 71.1 | 64 | 47 | 14.259 | 3.942 | 47.6 |
| 9 | 9A-34894 | 71.1 | 55 | 56 | 14.491 | 4.049 | 50.4 |
| 9 | 9A-34894 | 71.1 | 57 | 35 | 14.494 | 4.023 | 50.4 |
| 10 | 4057-201 | 82.1 | N/S | N/S | N/S | N/S | N/S |
| 11 | 4057-201 | 82.1 | 60 | 34 | 14.595 | 14.497 | 48.7 |
| 12 | 4057-201 | 82.1 | 63 | 55 | 4.032 | 4.063 | 48.4 |
| 13 | 4057-201 | 82.1 | N/S | N/S | N/S | N/S | N/S |
| 14 | 4057-201 | 82.1 | N/S | N/S | N/S | N/S | N/S |
| 15 | 4057-201 | 82.1 | N/S | N/S | N/S | N/S | N/S |
| 16 | 4125-039 | 87.8 | 54 | 32 | 14.888 | 4.179 | 53.0 |
| 17 | 4125-039 | 87.8 | 58 | 32 | 15.110 | 4.217 | 53.4 |

TABLE 4-continued

Methacrylic anhydride synthesized Ma2D37 and Lens Property Data (95:5)

| Example | Ma2D37 Lot | Ma2D37 Concentration | Lens Modulus | Lens CBCA | Lens Diameter | Lens Sag | Lens WC % |
|---|---|---|---|---|---|---|---|
| 18 | 4125-039 | 87.8 | 62 | 35 | 15.055 | 4.182 | 53.0 |
| 19 | 4125-039 | 87.8 | 71 | 45 | 15.045 | 4.215 | 51.5 |
| 20 | 4125-039 | 87.8 | 83 | 53 | 14.970 | 4.152 | 49.9 |

EXAMPLE 21-32

Preparation of a contact lens.

A monomer mixture was made by mixing the following components, in amounts of parts by weight, together with the polysiloxane prepolymer obtained in Example 3, as set forth below in Table 5.

TABLE 5

| Ex. | TRIS | Ma2D37 93:7 | NVP | HEMA | DMA | M1EDS6 | BPA-1 | CIX-4 | Monomer Mix (total) | Irgacure 819 | Visibility Tint | Hexanol |
|---|---|---|---|---|---|---|---|---|---|---|---|---|
| 21 | 36.52 | 7.4 | 32.34 | 4.97 | 4.97 | 13.29 | 0 | 0 | 99.49 | 0.5 | 0.02 | 7.5 |
| 22 | 36.52 | 7.4 | 32.34 | 4.97 | 4.97 | 13.29 | 0 | 0.1 | 99.59 | 0.5 | 0.02 | 7.5 |
| 23 | 36.52 | 7.4 | 32.34 | 4.97 | 4.97 | 13.29 | 0 | 0.2 | 99.69 | 0.5 | 0.02 | 7.5 |
| 24 | 36.52 | 7.4 | 32.34 | 4.97 | 4.97 | 13.29 | 0 | 0.3 | 99.79 | 0.5 | 0.02 | 7.5 |
| 25 | 36.52 | 7.4 | 32.34 | 4.97 | 4.97 | 13.29 | 0 | 0.4 | 99.89 | 0.5 | 0.02 | 7.5 |
| 26 | 36.52 | 7.4 | 32.34 | 4.97 | 4.97 | 13.29 | 0 | 0.5 | 99.99 | 0.5 | 0.02 | 7.5 |
| 27 | 36.52 | 7.4 | 32.34 | 4.97 | 4.97 | 13.29 | 0 | 0.6 | 100.09 | 0.5 | 0.02 | 7.5 |
| 28 | 30 | 7.4 | 38 | 4 | 4 | 13.3 | 1 | 0.0 | 97.70 | 0.5 | 0.02 | 7.5 |
| 29 | 30 | 7.4 | 38 | 4 | 4 | 13.3 | 1 | 0.1 | 97.80 | 0.5 | 0.02 | 7.5 |
| 30 | 30 | 7.4 | 38 | 4 | 4 | 13.3 | 1 | 0.2 | 97.90 | 0.5 | 0.02 | 7.5 |
| 31 | 30 | 7.4 | 38 | 4 | 4 | 13.3 | 1 | 0.4 | 98.10 | 0.5 | 0.02 | 7.5 |
| 32 | 30 | 7.4 | 38 | 4 | 4 | 13.3 | 1 | 0.6 | 98.30 | 0.5 | 0.02 | 7.5 |

The resultant monomeric mixture was cast into contact lenses by introducing the monomer mixture to a polypropylene mold assembly. Then, the mold assembly and monomer mixture were polymerized at 421 nm for 25 minutes at 5 mW/cm² to form a contact lens. The resultant contact lenses were released from the mold assembly. The contact lenses were extracted using the following process: 10 minutes in 50% isopropyl alcohol, 30 minutes in 100% isopropyl alcohol, 10 minutes in 50% isopropyl alcohol, 10 minutes in distilled water, and 10 minutes distilled water.

Next, the lens obtained were characterized by standard testing procedures as set forth below in Table 6. The Ma2D37s used in the lens formulations set forth in Table 6 were synthesized using methacrylic anhydride and acetic anhydride to form a dead end (i.e., non-reactive end) of the polymer.

TABLE 6

Methacrylic anhydride synthesized Ma2D37 and Lens Property (93:7)

| Example | Ma2D37 Lot (93:7) | Ma2D37 Concentration | Lens Modulus | Lens CBCA | Lens Diameter | Lens Sag | Lens WC % |
|---|---|---|---|---|---|---|---|
| 21 | 4057-125 | 73.0 | 64 | 47 | 14.438 | 3.967 | 49.0 |
| 21 | 4057-125 | 73.0 | 71 | 35 | 14.339 | 3.968 | 48.1 |

TABLE 6-continued

Methacrylic anhydride synthesized Ma2D37 and Lens Property (93:7)

| Example | Ma2D37 Lot (93:7) | Ma2D37 Concentration | Lens Modulus | Lens CBCA | Lens Diameter | Lens Sag | Lens WC % |
|---|---|---|---|---|---|---|---|
| 21 | 4057-129 | 77.8 | 59 | 35 | 14.392 | 4.019 | 49.3 |
| 21 | 4057-129 | 77.8 | 61 | 34 | 14.394 | 3.930 | 49.7 |
| 21 | 4057-129 | 77.8 | 54 | 34 | 14.335 | 4.033 | 50.0 |
| 21 | 4057-162 | 69.3 | 53 | 35 | 14.407 | 4.047 | 50.3 |
| 21 | 4057-163 | 65.0 | 56 | 34 | 14.270 | 4.024 | 49.2 |
| 21 | 4057-197 | 70.4 | 66 | 49 | 14.331 | 4.068 | 47.0 |
| 21 | 4057-202 | 86.0 | 62 | 36 | 14.513 | 4.076 | 48.7 |
| 21 | 4057-202 | 86.0 | 66 | 36 | 14.517 | 4.058 | 48.7 |
| 22 | 4057-202 | 86.0 | 60 | 41 | 14.406 | 4.007 | 50.8 |
| 23 | 4057-202 | 86.0 | 71 | 52 | 14.427 | 4.012 | 46.8 |
| 24 | 4057-202 | 86.0 | N/S | N/S | N/S | N/S | N/S |
| 25 | 4057-202 | 86.0 | N/S | N/S | N/S | N/S | N/S |
| 26 | 4057-202 | 86.0 | N/S | N/S | N/S | N/S | N/S |
| 27 | 4057-202 | 86.0 | N/S | N/S | N/S | N/S | N/S |
| 28 | 4125-022 | 79.6 | 50 | 33 | 15.048 | 4.175 | 56.0 |
| 29 | 4125-022 | 79.6 | 49 | 33 | 15.299 | 4.500 | 56.9 |
| 30 | 4125-022 | 79.6 | 57 | 35 | 15.314 | 4.265 | 55.4 |
| 31 | 4125-022 | 79.6 | 61 | 41 | 15.159 | 4.254 | 54.7 |
| 32 | 4125-022 | 79.6 | 73 | 60 | 15.253 | 4.212 | 53.1 |

EXAMPLE 33-39

Preparation of a contact lens.

A monomer mixture is made by mixing the following components, in amounts of parts by weight, together with the polysiloxane prepolymer obtained in Example 4 (Example 4 is 90:10), as set forth below in Table 7.

TABLE 7

| Ex. | TRIS | Ma2D37 92:8 | NVP | HEMA | DMA | M1EDS6 | CIX-4 | Monomer Mix (total) | Irgacure 819 | Visibility Tint | Hexanol |
|---|---|---|---|---|---|---|---|---|---|---|---|
| 33 | 36.52 | 7.4 | 32.34 | 4.97 | 4.97 | 13.29 | 0 | 99.49 | 0.5 | 0.02 | 7.5 |
| 34 | 36.52 | 7.4 | 32.34 | 4.97 | 4.97 | 13.29 | 0.1 | 99.59 | 0.5 | 0.02 | 7.5 |
| 35 | 36.52 | 7.4 | 32.34 | 4.97 | 4.97 | 13.29 | 0.2 | 99.69 | 0.5 | 0.02 | 7.5 |
| 36 | 36.52 | 7.4 | 32.34 | 4.97 | 4.97 | 13.29 | 0.3 | 99.79 | 0.5 | 0.02 | 7.5 |
| 37 | 36.52 | 7.4 | 32.34 | 4.97 | 4.97 | 13.29 | 0.4 | 99.89 | 0.5 | 0.02 | 7.5 |
| 38 | 36.52 | 7.4 | 32.34 | 4.97 | 4.97 | 13.29 | 0.5 | 99.99 | 0.5 | 0.02 | 7.5 |
| 39 | 36.52 | 7.4 | 32.34 | 4.97 | 4.97 | 13.29 | 0.6 | 100.09 | 0.5 | 0.02 | 7.5 |

The resultant monomeric mixture was cast into contact lenses by introducing the monomer mixture to a polypropylene mold assembly. Then, the mold assembly and monomer mixture were polymerized at 421 nm for 25 minutes at 5 mW/cm² to form a contact lens. The resultant contact lenses were released from the mold assembly. The contact lenses were extracted using the following process: 10 minutes in 50% isopropyl alcohol, 30 minutes in 100% isopropyl alcohol, 10 minutes in 50% isopropyl alcohol, 10 minutes in distilled water, and 10 minutes distilled water.

Next, the lens obtained were characterized by standard testing procedures as set forth below in Table 8. The Ma2D37s used in the lens formulations set forth in Table 8 were synthesized using methacrylic anhydride and acetic anhydride to form a non-reactive end of the polymer.

TABLE 8

Methacrylic anhydride synthesized Ma2D37 and Lens Property (92:8)

| Example | Ma2D37 Lot (92:8) | Ma2D37 Concentration | Lens Modulus | Lens CBCA | Lens Diameter | Lens Sag | Lens WC % |
|---|---|---|---|---|---|---|---|
| 33 | 9E-35839 | 83.5 | 5 | 33 | 14.396 | 4.024 | 49 |
| 34 | 9E-35839 | 83.5 | N/S | N/S | N/S | N/S | N/S |
| 35 | 9E-35839 | 83.5 | 52 | 37 | 14.619 | 4.019 | 51.2 |
| 36 | 9E-35839 | 83.5 | 49 | 43 | 14.779 | 3.979 | 51.7 |
| 37 | 9E-35839 | 83.5 | 65 | 54 | 14.578 | 4.010 | 48.7 |
| 38 | 9E-35839 | 83.5 | N/S | N/S | N/S | N/S | N/S |
| 39 | 9E-35839 | 83.5 | N/S | N/S | N/S | N/S | N/S |

EXAMPLE 40-46

Preparation of a contact lens.

A monomer mixture is made by mixing the following components, in amounts of parts by weight, together with the polysiloxane prepolymer obtained in Example 4, as set forth below in Table 9.

TABLE 9

| Ex. | TRIS | Ma2D37 90:10 | NVP | HEMA | DMA | M1EDS6 | CIX-4 | Monomer Mix (total) | Irgacure 819 | Visibility Tint | Hexanol |
|---|---|---|---|---|---|---|---|---|---|---|---|
| 40 | 36.52 | 7.4 | 32.34 | 4.97 | 4.97 | 13.29 | 0.0 | 99.49 | 0.5 | 0.02 | 7.5 |
| 41 | 36.52 | 7.4 | 32.34 | 4.97 | 4.97 | 13.29 | 0.1 | 99.59 | 0.5 | 0.02 | 7.5 |
| 42 | 36.52 | 7.4 | 32.34 | 4.97 | 4.97 | 13.29 | 0.2 | 99.69 | 0.5 | 0.02 | 7.5 |
| 43 | 36.52 | 7.4 | 32.34 | 4.97 | 4.97 | 13.29 | 0.3 | 99.79 | 0.5 | 0.02 | 7.5 |
| 44 | 36.52 | 7.4 | 32.34 | 4.97 | 4.97 | 13.29 | 0.4 | 99.89 | 0.5 | 0.02 | 7.5 |
| 45 | 36.52 | 7.4 | 32.34 | 4.97 | 4.97 | 13.29 | 0.5 | 99.99 | 0.5 | 0.02 | 7.5 |
| 46 | 36.52 | 7.4 | 32.34 | 4.97 | 4.97 | 13.29 | 0.6 | 100.09 | 0.5 | 0.02 | 7.5 |

The resultant monomeric mixture was cast into contact lenses by introducing the monomer mixture to a polypropylene mold assembly. Then, the mold assembly and monomer mixture were polymerized at 421 nm for 25 minutes at 5 mW/cm² to form a contact lens. The resultant contact lenses were released from the mold assembly. The contact lenses were extracted using the following process: 10 minutes in 50% isopropyl alcohol, 30 minutes in 100% isopropyl alcohol, 10 minutes in 50% isopropyl alcohol, 10 minutes in distilled water, and 10 minutes distilled water.

Next, the lens obtained were characterized by standard testing procedures as set forth below in Table 10. The Ma2D37s used in the lens formulations set forth in Table 10 were synthesized using methacrylic anhydride and acetic anhydride to form a non-reactive end of the polymer.

TABLE 10

Methacrylic anhydride synthesized Ma2D37 and Lens Property Data (90:10)

| Example | Ma2D37 Lot (90:10) | Ma2D37 Concentration | Lens Modulus | Lens CBCA | Lens Diameter | Lens Sag | Lens WC % |
|---|---|---|---|---|---|---|---|
| 40 | 4057-211 | 83.2 | 55 | 33 | 14.434 | 4.022 | 49.5 |
| 40 | 4057-213 | 79.3 | 57 | 33 | 14.424 | 4.132 | 49.0 |
| 40 | 4043-104 | 76.4 | 56 | 37 | 14.417 | 3.930 | 48.1 |
| 40 | 4057-76 | 74.4 | 58 | 37 | 14.487 | 3.929 | 48.6 |
| 40 | 8H-33754 | 70.8 | 60 | 33 | 14.258 | 3.955 | 49.0 |
| 40 | 8H-33754 | 70.8 | 62 | 33 | 14.199 | 3.937 | 49.2 |
| 40 | 8H-33754 | 70.8 | 59 | 39 | 14.301 | 3.931 | 49.5 |
| 40 | 8H-33754 | 70.8 | 60 | 36 | 14.036 | 3.972 | 49.6 |
| 40 | 8H-33754 | 70.8 | 60 | 34 | 14.400 | 3.981 | 49.4 |
| 41 | 8H-33754 | 70.8 | N/S | N/S | N/S | N/S | N/S |
| 42 | 8H-33754 | 70.8 | 53 | 40 | 14.545 | 4.058 | 51.0 |
| 43 | 8H-33754 | 70.8 | 59 | 45 | 14.549 | 4.028 | 50.1 |
| 44 | 8H-33754 | 70.8 | 73 | 58 | 14.444 | 4.013 | 47.2 |
| 45 | 8H-33754 | 70.8 | N/S | N/S | N/S | N/S | N/S |
| 46 | 8H-33754 | 70.8 | N/S | N/S | N/S | N/S | N/S |

EXAMPLE 47

Preparation of a contact lens.

A monomer mixture was made by mixing the following components, in amounts of parts by weight, together with the polysiloxane prepolymer obtained in Example 4 (Example 4 is 90:10 Acetamide), as set forth below in Table 11.

TABLE 11

| Ingredient | Parts by Weight |
|---|---|
| Ma2D37 of Example 4 | 7.4 |
| TRIS | 36.52 |
| NVP | 32.34 |
| HEMA | 4.97 |
| DMA | 4.97 |
| M1EDS6 | 13.29 |
| Monomer Mix (total) | 99.49 |
| Hexanol | 7.5 |
| Irgacure 819 | 0.5 |
| Tint | 0.02 |

The resultant monomeric mixture was cast into contact lenses by introducing the monomer mixture to a polypropylene mold assembly. Then, the mold assembly and monomer mixture were polymerized at 421 nm for 25 minutes at 5 mW/cm² to form a contact lens. The resultant contact lenses were released from the mold assembly. The contact lenses were extracted using the following process: 10 minutes in 50% isopropyl alcohol, 30 minutes in 100% isopropyl alcohol, 10 minutes in 50% isopropyl alcohol, 10 minutes in distilled water, and 10 minutes distilled water.

Next, the lens obtained were characterized by standard testing procedures as set forth below in Table 12. The Ma2D37s used in the lens formulations set forth in Table 12 were synthesized using methacrylic anhydride and acetic anhydride. Alternative dead end groups were used at different feed ratios to form a non-reactive end of the polymer.

TABLE 12

Methacrylic anhydride synthesized Ma2D37 and Lens Property Data Using Alternative Non-Reactive End Functionality.

| Example | Ma2D37 Lot | Non-Reactive Functional Group | Ma2D37 Concentration | Lens Modulus | Lens CBCA | Lens Diameter | Lens Sag | Lens WC % |
|---|---|---|---|---|---|---|---|---|
| 47 | 4057-181 | Valeric | 80.2 | 63 | 35 | 14.370 | 3.963 | 47.3 |
| 47 | 4057-214 | Valeric | 83.3 | 57 | 32 | 14.327 | 3.986 | 48.5 |
| 47 | 4057-177 | Octyl | 79.0 | 55 | 46 | 14.316 | 3.950 | 48.1 |
| 47 | 4057-177 | Octyl | 79.0 | 59 | 36 | 14.211 | 3.984 | 48.7 |
| 47 | 4057-188 | Octyl | 75.9 | 63 | 40 | 14.256 | 3.974 | 48.2 |
| 47 | 4125-001 | Octyl | 85.8 | 54 | 38 | 14.393 | 4.011 | 50.2 |
| 47 | 4125-002 | Octyl | 86.7 | 58 | 42 | 14.355 | 4.010 | 48.7 |
| 47 | 4057-200 | Dodecyl | 80.3 | 56 | 35 | 14.443 | 4.008 | 50.0 |
| 47 | 4057-176 | Cyclopentyl | 81.2 | 65 | 35 | 14.269 | 3.932 | 48.0 |
| 47 | 4057-180 | Cyclohexyl | 80.3 | 61 | 37 | 14.270 | 3.963 | 48.3 |
| 47 | 4057-198 | Cyclohexyl | 84.9 | 68 | 48 | 14.256 | 3.981 | 47.4 |
| 47 | 4057-187 | Benzoic | 76.6 | 65 | 39 | 14.319 | 3.970 | 47.7 |

EXAMPLE 48

Preparation of a contact lens.

A monomer mixture was made by mixing the following components, in amounts of parts by weight, together with the polysiloxane prepolymer obtained in Example 6, as set forth below in Table 13.

TABLE 13

| Ingredient | Parts by Weight |
|---|---|
| Ma2D37 of Example 6 | 7.4 |
| TRIS | 36.52 |
| NVP | 32.34 |
| HEMA | 4.97 |
| DMA | 4.97 |
| M1EDS6 | 13.29 |
| Monomer Mix (total) | 99.49 |
| Hexanol | 7.5 |
| Irgacure 819 | 0.5 |
| Tint | 0.02 |

The resultant monomeric mixture was cast into contact lenses by introducing the monomer mixture to a polypropylene mold assembly. Then, the mold assembly and monomer mixture were polymerized at 421 nm for 25 minutes at 5 mW/cm² to form a contact lens. The resultant contact lenses were released from the mold assembly. The contact lenses were extracted using the following process: 10 minutes in 50% isopropyl alcohol, 30 minutes in 100% isopropyl alcohol, 10 minutes in 50% isopropyl alcohol, 10 minutes in distilled water, and 10 minutes distilled water.

Next, the lens obtained were characterized by standard testing procedures as set forth below in Table 14.

TABLE 14

IEM synthesized Ma2D37 and Lens Property Data (100:0).

| Example | Ma2D37 Lot | Ma2D37 Concentration | Lens Modulus | Lens CBCA | Lens Diameter | Lens Sag | Lens WC % |
|---|---|---|---|---|---|---|---|
| 48 | 4041-123 | 69% (Calculated from ¹H NMR) | 86 | 51 | 14.148 | 3.848 | 44.5 |

EXAMPLE 49

Preparation of a contact lens.

A monomer mixture was made by mixing the following components, in amounts of parts by weight, together with the polysiloxane prepolymer obtained in Example 7, as set forth below in Table 15.

TABLE 15

| Ingredient | Parts by Weight |
|---|---|
| Ma2D37 of Example 7 | 7.4 |
| TRIS | 36.52 |
| NVP | 32.34 |
| HEMA | 4.97 |
| DMA | 4.97 |
| M1EDS6 | 13.29 |
| Monomer Mix (total) | 99.49 |
| Hexanol | 7.5 |
| Irgacure 819 | 0.5 |
| Tint | 0.02 |

The resultant monomeric mixture was cast into contact lenses by introducing the monomer mixture to a polypropylene mold assembly. Then, the mold assembly and monomer mixture were polymerized at 421 nm for 25 minutes at 5 mW/cm² to form a contact lens. The resultant contact lenses were released from the mold assembly. The contact lenses were extracted using the following process: 10 minutes in 50% isopropyl alcohol, 30 minutes in 100% isopropyl alcohol, 10 minutes in 50% isopropyl alcohol, 10 minutes in distilled water, and 10 minutes distilled water.

Next, the lens obtained were characterized by standard testing procedures as set forth below in Table 16. The Ma2D37s used in the lens formulations set forth in Table 16 were synthesized using methacrylic anhydride and alternative end groups that have varying degrees of hydrophobicity.

TABLE 16

Methacrylic anhydride synthesized Ma2D37 and Lens Property Data with Urea Non-Reactive End Functionality

| Example | Ma2D37 Lot | Urea Functional Group | Ma2D37 Concentration | Lens Modulus | Lens CBCA | Lens Diameter | Lens Sag | Lens WC % |
|---|---|---|---|---|---|---|---|---|
| 49 | 4041-134 | Propyl | 88.3 | 66 | 49 | 14.264 | 3.996 | 47.2 |
| 49 | 4041-134 | Propyl | 88.3 | 57 | 45 | 14.4862 | 4.106 | 50.4 |
| 49 | 4041-174 | Valeric | 88.3 | 60 | 34 | 14.224 | 3.943 | 48.1 |
| 49 | 4041-136 | Octyl | 79.5 | 52 | 51 | 14.308 | 3.941 | 50.4 |
| 49 | 4041-151 | Octyl | 75.5 | 60 | 41 | 14.312 | 3.999 | 48.8 |
| 49 | 4041-154 | Octyl | 73.4 | 51 | 34 | 14.570 | 4.075 | 48.3 |
| 49 | 4041-138 | Cyclohexyl | 84.9 | 64 | 40 | 14.312 | 3.963 | 48.3 |

TABLE 16-continued

Methacrylic anhydride synthesized Ma2D37 and Lens Property Data with Urea Non-Reactive End Functionality

| Example | Ma2D37 Lot | Urea Ma2D37 Functional Group | Ma2D37 Concentration | Lens Modulus | Lens CBCA | Lens Diameter | Lens Sag | Lens WC % |
|---|---|---|---|---|---|---|---|---|
| 49 | 4041-155 | Cyclohexyl | 78.1 | 60 | 34 | 14.441 | 4.029 | 50.2 |

It will be understood that various modifications may be made to the embodiments disclosed herein. Therefore the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the features and advantages appended hereto.

What is claimed is:

1. A method comprising the steps of:
(a) reacting a polysiloxane prepolymer having reactive functional end groups with a non-free radical polymerizable reactive end-capping agent, wherein the non-free radical polymerizable reactive end-capping agent is one of a carbonyl-containing non-free radical polymerizable reactive end-capping agent of the general formula:

wherein $R^8$ is a non-reactive moiety and C(O)X is a non-free radical polymerizable reactive group, or a chloroformate of the general formula:

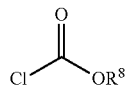

wherein $R^8$ has the aforestated meaning; and
(b) reacting the reaction product of step (a) with a free-radical polymerizable reactive end-capping agent.

2. The method of claim 1, wherein the polysiloxane prepolymer is of formula I:

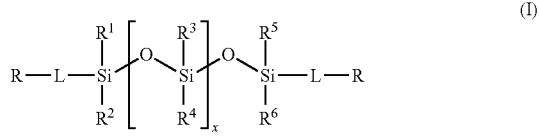

(I)

wherein each R is an independently reactive functional end group, $R^1$ to $R^6$ are independently straight or branched, substituted or unsubstituted $C_1$-$C_{30}$ alkyl group, a substituted or unsubstituted $C_3$-$C_{30}$ cycloalkyl group, a substituted or unsubstituted $C_4$-$C_{30}$ cycloalkylalkyl group, a substituted or unsubstituted $C_3$-$C_{30}$ cycloalkenyl group, a substituted or unsubstituted $C_6$-$C_{30}$ aryl group, and a substituted or unsubstituted $C_7$-$C_{30}$ arylalkyl group, and L is independently a linking group.

3. The method of claim 2, wherein the reactive functional end group includes the same or different reactive functional end group selected from the group consisting of a hydroxyl-containing reactive functional end group and an amine-containing reactive functional end group.

4. The method of claim 1, wherein the reactive functional end group is —OH.

5. The method of claim 1, wherein the reactive functional end group is an amine-containing reactive functional end group of the general formula —$NHR^7$ wherein $R^7$ is independently hydrogen, an alkyl group, an aryl group, and a cycloalkyl group.

6. The method of claim 1, wherein the L linking group is independently a straight or branched alkyl group, cycloalkyl group, an aryl group, an ether or polyether group, and an ester group.

7. The method of Claim 1, wherein $R^8$ is selected from the group consisting of $C_1$ to $C_{18}$ alkyl groups, $C_3$ to $C_{18}$ cycloalkyl groups and $C_6$ to $C_{18}$ aryl groups and X is selected from the group consisting of —OH, halogen and —$OR^9$ wherein $R^9$ is a substituted or unsubstituted heteroaryl or —$C(O)R^8$ wherein le has the aforestated meanings.

8. The method of claim 1, wherein the non-free radical polymerizable reactive end-capping agent is reacted with the polysiloxane prepolymer in an amount ranging from about 3 to about 15 mole % of non-free radical polymerizable reactive end-capping agent per mole of end groups in the polymer.

9. The method of claim 1, wherein the non-free radical polymerizable reactive end-capping agent is reacted with the polysiloxane prepolymer in an amount ranging from about 1 to about 30 mole % of non-free radical polymerizable reactive end-capping agent per mole of end groups in the polymer.

10. The method of claim 1, wherein the non-free radical polymerizable reactive end-capping agent is reacted with the polysiloxane prepolymer at a temperature ranging from about 0° C. to about 40° C.

11. The method of claim 1, wherein the free radical polymerizable reactive end-capping agent is a free radical polymerizable reactive end-capping agent having at least one ethylenically unsaturated reactive end group.

12. The method of claim 1, wherein the free radical polymerizable reactive end-capping agent is selected from the group consisting of a (meth)acrylate-containing free radical polymerizable reactive end-capping agent, a vinyl-containing free radical polymerizable reactive end-capping agent, an unsaturated acidic-containing free radical polymerizable reactive end-capping agent and a styryl-containing free radical polymerizable reactive end-capping agent.

13. The method of claim 12, wherein the free radical polymerizable reactive end-capping agent is a (meth)acrylate-containing free radical polymerizable reactive end-capping agent selected from the group consisting of a symmetrical (meth)acrylate-containing acid anhydride free radical polymerizable reactive end-capping agent, a (meth)acrylate-containing acid chloride free radical polymerizable reactive end-capping agent, a (meth)acrylate-containing carboxylic acid free radical polymerizable reactive end-capping agent, a (meth)acrylate-containing carbonyl-containing free radical polymerizable reactive end-capping agent, and a (meth)acrylate-containing isocyanate- containing free radical polymerizable reactive end-capping agent.

14. The method of claim 12, wherein the free radical polymerizable reactive end-capping agent is a vinyl-containing free radical polymerizable reactive end-capping agent selected from the group consisting of a vinyl isocyanate free radical polymerizable reactive end-capping agent, and a vinyl chloroformate free radical polymerizable reactive end-capping agent.

15. The method of claim 12, wherein the free radical polymerizable reactive end-capping agent is an unsaturated acidic-containing free radical polymerizable reactive end-capping agent which is maleic anhydride.

16. The method of claim 1, wherein the free radical polymerizable reactive end-capping agent is reacted with the product of step (a) in an excess amount.

17. The method of claim 1, wherein the free radical polymerizable reactive end- capping agent is reacted with the product of step (a) at a temperature ranging from about 0° C. to about 40° C.

18. The method of claim 1, wherein the product of step (b) is further reacted with one or more biomedical-device forming monomers to obtain a biomedical device.

19. The method of claim 18, wherein the biomedical device is an ophthalmic lens.

20. The method of claim 18, wherein the biomedical device is a contact lens.

21. The method of claim 18, wherein the biomedical device is an intraocular lens.

22. The method of claim 1, wherein the carbonyl-containing non-free radical polymerizable reactive end-capping agent is represented by a structure of the general formula:

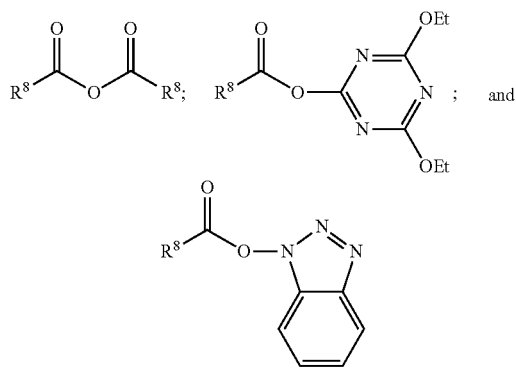

wherein $R^8$ has the aforestated meaning.

23. The method of claim 1, wherein the reaction of the non-free radical polymerizable reactive end-capping agent with the polysiloxane prepolymer is carried out in the presence of a solvent.

* * * * *

UNITED STATES PATENT AND TRADEMARK OFFICE
CERTIFICATE OF CORRECTION

PATENT NO. : 10,870,731 B2
APPLICATION NO. : 16/246715
DATED : December 22, 2020
INVENTOR(S) : Ivan M. Nuñez et al.

It is certified that error appears in the above-identified patent and that said Letters Patent is hereby corrected as shown below:

In the Claims

Claim 4, Column 38, Line 23, delete "claim 1" and insert therefor --claim 2--

Claim 5, Column 38, Line 25, delete "claim 1" and insert therefor --claim 2--

Claim 6, Column 38, Line 23, delete "claim 1" and insert therefor --claim 2--

Claim 7, Column 38, Line 40, delete "wherein le" and insert therefor --wherein $R^8$--

Claim 17, Column 38, Line 23, delete "end- capping" and insert therefor --end-capping--

Signed and Sealed this
Sixteenth Day of February, 2021

Drew Hirshfeld
*Performing the Functions and Duties of the*
*Under Secretary of Commerce for Intellectual Property and*
*Director of the United States Patent and Trademark Office*